(12) United States Patent
Nelson et al.

(10) Patent No.: US 8,741,598 B2
(45) Date of Patent: Jun. 3, 2014

(54) PHOTOCATALYTIC HYDROGEN PRODUCTION IN CYANOBACTERIA

(71) Applicant: Ramot at Tel-Aviv University Ltd., Tel-Aviv (IL)

(72) Inventors: Nathan Nelson, Tel-Aviv (IL); Iftach Yacoby, Kfar-Hess (IL); Ehud Gazit, Ramat-HaSharon (IL); Itai Benhar, Rehovot (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 14/055,895

(22) Filed: Oct. 17, 2013

(65) Prior Publication Data

US 2014/0106428 A1    Apr. 17, 2014

Related U.S. Application Data

(62) Division of application No. 13/322,171, filed as application No. PCT/IL2010/000419 on May 26, 2010, now Pat. No. 8,563,294.

(60) Provisional application No. 61/213,289, filed on May 26, 2009.

(51) Int. Cl.
    *C12P 1/00* (2006.01)
(52) U.S. Cl.
    USPC .......................................................... 435/41
(58) Field of Classification Search
    None
    See application file for complete search history.

(56) References Cited

U.S. PATENT DOCUMENTS

2012/0115202 A1    5/2012   Nelson et al.

FOREIGN PATENT DOCUMENTS

| WO | WO 03/067213 | 8/2003 |
| WO | WO 2009/013745 | 1/2009 |

OTHER PUBLICATIONS

International Search Report and the Written Opinion Dated Aug. 10, 2010 From the International Searching Authority Re. Application No. PCT/IL2010/000419.
Official Action Dated Feb. 26, 2013 From the US Patent and Trademark Office Re. U.S. Appl. No. 13/322,171.
Dinsdale et al. "Microbial Ecology of Four Coral Atolls in the Northern Line Islands", PLos ONE, XP002594174, 3(2/c1584): Feb. 1-17, 2008.
Fischer et al. "A Large Fraction of PsaF is Nonfunctional in Photosystem I Complexes Lacking the PsaJ Subunit", Biochemistry, XP002594175, 38(17): 5546-5552, Apr. 27, 1999. EDC Cross-Linked PsaF-J, p. 5546, col. 2.
Kruip et al. "Structural Organization of the Major Subunits in Cyanobacterial Photosystem I", The Journal of Biological Chemistry, XP002456426, 272(27): 17061-17069, Jul. 4, 1997. EDC Cross-Linked PsaF-J, Abstract.
Sharon et al. "Photosystem I Gene Cassettes Are Present in Marine Virus Genomes", Nature, XP002594172, 461(7261): 258-262, Sep. 10, 2009. PsaJF Fusion, Abstract, p. 260, col. 1.
Sharon et al. "SubName: Full=PsaJF", Database UniProt [Online], XP002594173, Retrieved From EBI Accession No. UNIPROT:B7T4D2, Database Accession No. B7T4D2, Feb. 10, 2009. Phage Natural PsaF-PsaJ Fusion Peptide (Coding DNA Also Known But Not Shown here)Compound.

*Primary Examiner* — Nashaat Nashed

(57) ABSTRACT

A cyanobacterial cell comprising a PSI complex which accepts electrons from at least one respiratory cytochrome is disclosed. Methods of generating same and use of same for the production of hydrogen gas are also disclosed.

10 Claims, 9 Drawing Sheets
(8 of 9 Drawing Sheet(s) Filed in Color)

FIG. 1A
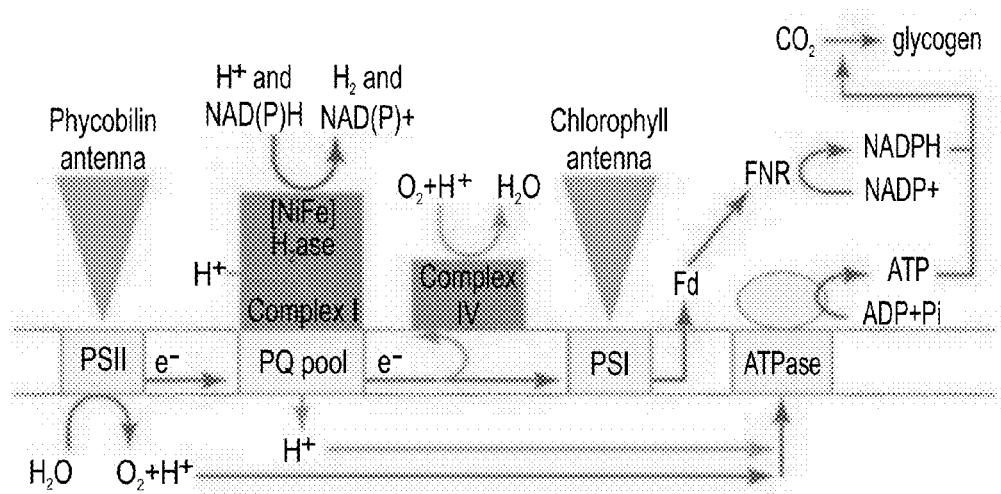
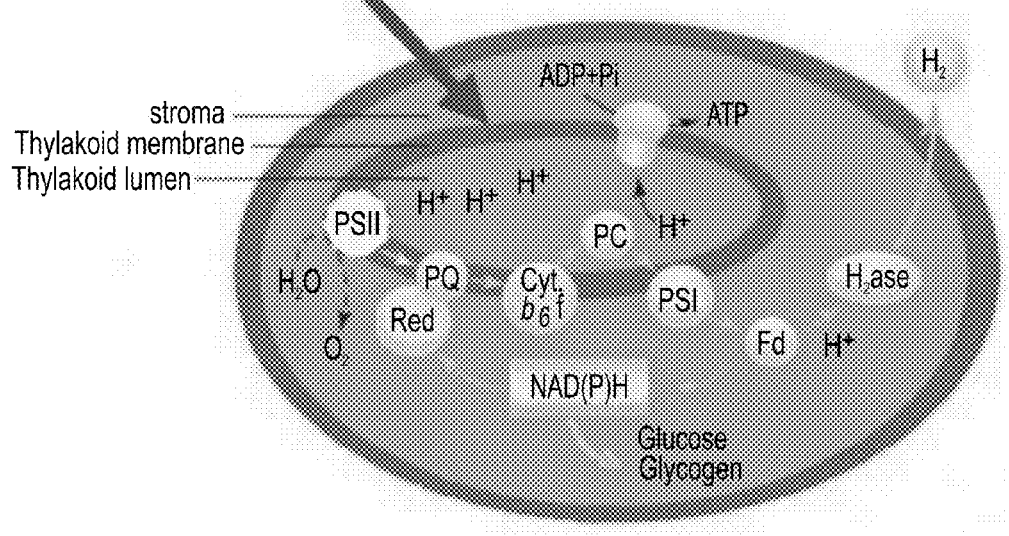
FIG. 1B

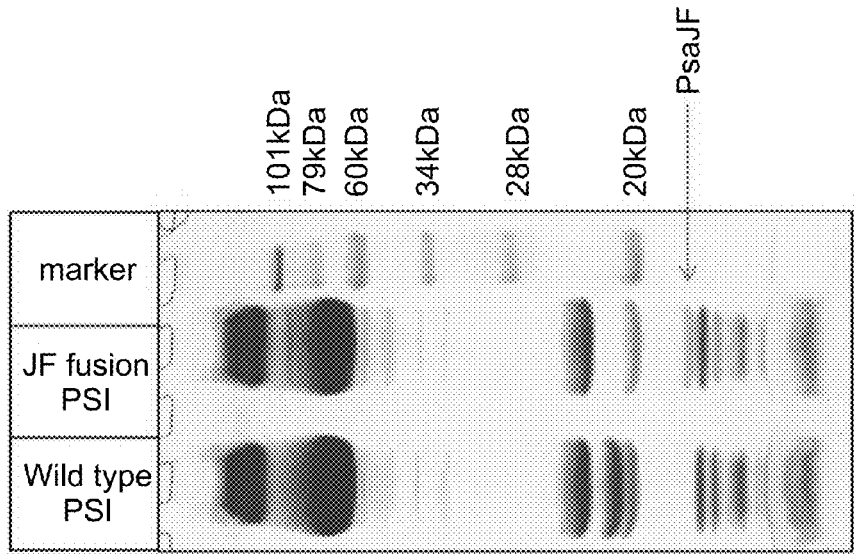
FIG. 5C
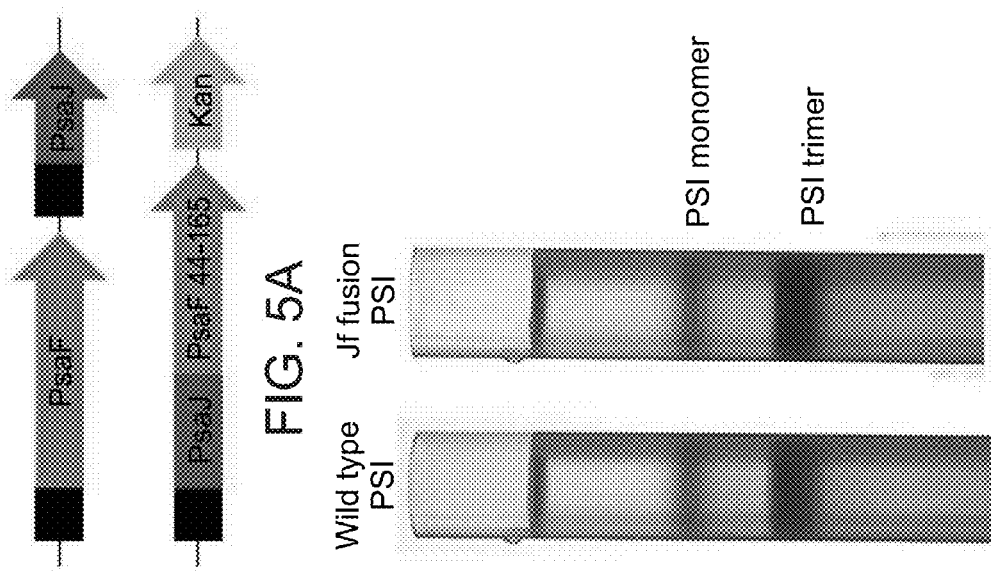
FIG. 5A
FIG. 5B

SEQUENCE LISTING

<160> NUMBER OF SEQ ID NOS: 26

<210> SEQ ID NO 1
<211> LENGTH: 125
<212> TYPE: PRT
<213> ORGANISM: Artificial sequence
<220> FEATURE:
<223> OTHER INFORMATION: PsaJF fusion protein

<400> SEQUENCE: 1

```
Met Asp Gly Leu Lys Ser Phe Leu Ser Thr Ala Pro Val Met Ile Met
1               5                   10                  15

Ala Leu Leu Thr Phe Thr Ala Gly Ile Leu Ile Glu Phe Asn Arg Phe
            20                  25                  30

Tyr Pro Asp Leu Leu Phe His Pro Cys Ser Cys Ala Gly Asp Phe Leu
            35                  40                  45

Ile Pro Ser Ile Leu Phe Leu Tyr Ile Ala Gly Trp Ile Gly Trp Val
50                  55                  60

Gly Arg Ser Tyr Leu Ile Glu Ile Arg Glu Ser Lys Asn Pro Glu Met
65                  70                  75                  80

Gln Glu Val Val Ile Asn Val Pro Leu Ala Ile Lys Lys Met Leu Gly
                85                  90                  95

Gly Phe Leu Trp Pro Leu Ala Ala Val Gly Glu Tyr Thr Ser Gly Lys
            100                 105                 110

Leu Val Met Lys Asp Ser Glu Ile Pro Thr Ser Pro Arg
            115                 120                 125

<210> SEQ ID NO 2
<211> LENGTH: 378
<212> TYPE: DNA
<213> ORGANISM: Artificial sequence
<220> FEATURE:
<223> OTHER INFORMATION: PsaJF fusion protein coding sequence

<400> SEQUENCE: 2
atggacggtt tgaaatcctt tttgtcaact gctccggtca tgatcatggc tttgttgact      60
ttcaccgctg gtattttgat cgagtttaat cgttttatc ccgatcttct tttccacccc     120
tgttcttgtg ctggtgactt tttgattcct agcattttgt tcctgtacat tgctggttgg    180
atcggctggg ttggtcgttc ttacctgatt gaaattcggg aaagcaaaaa tcctgaaatg    240
caggaagtgg ttattaatgt ccccctagcg atcaaaaaaa tgttgggtgg tttcctttgg    300
cccttggccg ccgttggtga atacacctcc ggcaaactgg tgatgaagga ttcagaaatc    360
cccacttccc cccgctaa                                                  378

<210> SEQ ID NO 3
<211> LENGTH: 40
<212> TYPE: PRT
<213> ORGANISM: Artificial sequence
<220> FEATURE:
<223> OTHER INFORMATION: An exemplary PsaJ amino acid sequence

<400> SEQUENCE: 3

Met Asp Gly Leu Lys Ser Phe Leu Ser Thr Ala Pro Val Met Ile Met
1               5                   10                  15

Ala Leu Leu Thr Phe Thr Ala Gly Ile Leu Ile Glu Phe Asn Arg Phe
            20                  25                  30

Tyr Pro Asp Leu Leu Phe His Pro
            35                  40

<210> SEQ ID NO 4
<211> LENGTH: 165
<212> TYPE: PRT
<213> ORGANISM: Artificial sequence
<220> FEATURE:
<223> OTHER INFORMATION: An exemplary PsaF amino acid sequence

<400> SEQUENCE: 4

Met Lys His Leu Leu Ala Leu Leu Leu Ala Phe Thr Leu Trp Phe Asn
1               5                   10                  15
```

```
Phe Ala Pro Ser Ala Ser Ala Asp Asp Phe Ala Asn Leu Thr Pro Cys
            20                  25                  30
Ser Glu Asn Pro Ala Tyr Leu Ala Lys Ser Lys Asn Phe Leu Asn Thr
        35                  40                  45
Thr Asn Asp Pro Asn Ser Gly Lys Ile Arg Ala Glu Arg Tyr Ala Ser
 50                  55                  60
Ala Leu Cys Gly Pro Glu Gly Tyr Pro His Leu Ile Val Asp Gly Arg
 65                  70                  75                  80
Phe Thr His Ala Gly Asp Phe Leu Ile Pro Ser Ile Leu Phe Leu Tyr
                85                  90                  95
Ile Ala Gly Trp Ile Gly Trp Val Gly Arg Ser Tyr Leu Ile Glu Ile
            100                 105                 110
Arg Glu Ser Lys Asn Pro Glu Met Gln Glu Val Val Ile Asn Val Pro
        115                 120                 125
Leu Ala Ile Lys Lys Met Leu Gly Gly Phe Leu Trp Pro Leu Ala Ala
130                 135                 140
Val Gly Glu Tyr Thr Ser Gly Lys Leu Val Met Lys Asp Ser Glu Ile
145                 150                 155                 160
Pro Thr Ser Pro Arg
                165
```

<210> SEQ ID NO 5
<211> LENGTH: 54
<212> TYPE: DNA
<213> ORGANISM: Artificial sequence
<220> FEATURE:
<223> OTHER INFORMATION: PsaF promoter

<400> SEQUENCE: 5
cttatttatt tagccgcctt tttagtcttt tgtttaacca aggaaacgat tctt        54

<210> SEQ ID NO 6
<211> LENGTH: 2378
<212> TYPE: DNA
<213> ORGANISM: Artificial sequence
<220> FEATURE:
<223> OTHER INFORMATION: PsaJF coding region flanking with regions
      complementary to the cyanobacterial genome for homologous
      recombination

<400> SEQUENCE: 6
gggcgaattg ggcccgacgt cgcatgctcc cggccgccat ggcggccgcg ggaattcgat     60
tgtaaatgct ggcgagaggc cacttccggt actacccgc cgaaaatttg atgggtttgt    120
atttgggaag aaaccacatt actgcaaacg ttacgattat ttacaattgc caccgcagtt   180
tcatcacaac ttgtttcaat tgctaaaatg attgccattc tctgctagtt tgagtttgat   240
ccaaaagacg acggtttatt agcccagtct ttcctattat cggctaacga tccccggatc   300
acggtaacag gttgcgaatc ttgcttattt atttagccgc cttttagtc ttttgtttaa   360
ccaaggaaac gattcttatg gacggtttga atccttttt gtcaactgct ccggtcatga   420
tcatggcttt gttgactttc accgctggta ttttgatcga gttaatcgt ttttatcccg    480
atcttctttt ccaccctgt tcttgtgctg gtgacttttt gattcctagc attttgttcc    540
tgtacattgc tggttggatc ggctgggttg gtcgttctta cctgattgaa attcgggaaa   600
gcaaaaatcc tgaaatgcag gaagtggtta ttaatgtccc cctagcgatc aaaaaaatgt    660
tgggtggttt cctttggccc ttggccgcg ttggtgaata cacctccggc aaactggtga    720
tgaaggattc agaaatcccc acttcccccc gctaattagt tgggcattga ctgcaggggg   780
```

-continued

```
ggggggggcgc tgaggtctgc ctcgtgaaga aggtgttgct gactcatacc aggcctgaat      840
cgccccatca tccagccaga aagtgaggga gccacggttg atgagagctt tgttgtaggt      900
ggaccagttg gtgattttga acttttgctt tgccacggaa cggtctgcgt tgtcgggaag      960
atgcgtgatc tgatccttca actcagcaaa agttcgattt attcaacaaa gccgccgtcc     1020
cgtcaagtca gcgtaatgct ctgccagtgt acaaccaat taaccaattc tgattagaaa      1080
aactcatcga gcatcaaatg aaactgcaat ttattcatat caggattatc aataccatat     1140
ttttgaaaaa gccgtttctg taatgaagga gaaaactcac cgaggcagtt ccataggatg     1200
gcaagatcct ggtatcggtc tgcgattccg actcgtccaa catcaataca acctattaat     1260
ttcccctcgt caaaaataag gttatcaagt gagaaatcac catgagtgac gactgaatcc     1320
ggtgagaatg gcaaaagctt atgcatttct ttccagactt gttcaacagg ccagccatta     1380
cgctcgtcat caaaatcact cgcatcaacc aaaccgttat tcattcgtga ttgcgcctga     1440
gcgagacgaa atacgcgatc gctgttaaaa ggacaattac aaacaggaat cgaatgcaac     1500
cggcgcagga acactgccag cgcatcaaca atattttcac ctgaatcagg atattcttct     1560
aatacctgga atgctgtttt cccggggatc gcagtggtga gtaaccatgc atcatcagga     1620
gtacggataa aatgcttgat ggtcggaaga ggcataaatt ccgtcagcca gtttagtctg     1680
accatctcat ctgtaacatc attggcaacg ctacctttgc catgtttcag aaacaactct     1740
ggcgcatcgg gcttcccata caatcgatag attgtcgcac ctgattgccc gacattatcg     1800
cgagcccatt tatacccata taatcagca tccatgttgg aatttaatcg cggcctcgag     1860
caagacgttt cccgttgaat atggctcata caccccttg tattactgtt tatgtaagca     1920
gacagtttta ttgttcatga tgatatattt ttatcttgtg caatgtaaca tcagagattt     1980
tgagacacaa cgtggctttc ccccccccc ctgcagaggt gagataaaag attggttggg     2040
atttgtaatt gagatcctag ccaatttttt ttggtaaaaa taactggatt aatcggttaa     2100
tttacctggg ttgagcaaat taaggggatc tacctggcgt ttaaaaatta attgggattc     2160
tggcagaggt tgtaccgacc ctccggctaa actataggtg tggggattgg cgattctggc     2220
ccctagattt tggtgggcgg ccatgatttc ttccaggcga tcaccgttga taaatcacta     2280
gtgaattcgc ggccgcctgc aggtcgacca tatgggagag ctcccaacgc gttggatgca     2340
tagcttgagt attctatagt gtcacctaaa tagcttgg                             2378

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
gtaaatgctg gcgagaggcc ac                                                 22

<210> SEQ ID NO 8
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 8
aagaatcgtt tccttggtta aaca                                               24
```

```
<210> SEQ ID NO 9
<211> LENGTH: 45
<212> TYPE: DNA
<213> ORGANISM: Artificial sequence
<220> FEATURE:
<223> OTHER INFORMATION: Single strand DNA oligonucleotide

<400> SEQUENCE: 9
tgtttaacca aggaaacgat tcttatggac ggtttgaaat cctttt          45

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10 acagggtgg aaaagaagat cg                                      22

<210> SEQ ID NO 11
<211> LENGTH: 54
<212> TYPE: DNA
<213> ORGANISM: Artificial sequence
<220> FEATURE:
<223> OTHER INFORMATION: Single strand DNA oligonucleotide

<400> SEQUENCE: 11
cccgatcttc ttttccaccc ctgttcttgt gctggtgact ttttgattcc tagc   54

<210> SEQ ID NO 12
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 12
gtccagtcaa tgcccaactg gttagcgg                               28

<210> SEQ ID NO 13
<211> LENGTH: 51
<212> TYPE: DNA
<213> ORGANISM: Artificial sequence
<220> FEATURE:
<223> OTHER INFORMATION: Single strand DNA oligonucleotide

<400> SEQUENCE: 13
ccgctaatta gttgggcatt gactgcaggt gagataaaag attggttggg a      51

<210> SEQ ID NO 14
<211> LENGTH: 122
<212> TYPE: PRT
<213> ORGANISM: Artificial sequence
<220> FEATURE:
<223> OTHER INFORMATION: Truncated PSAF amino acid sequence

<400> SEQUENCE: 14

Asn Phe Leu Asn Thr Thr Asn Asp Pro Asn Ser Gly Lys Ile Arg Ala
1               5                   10                  15

Glu Arg Tyr Ala Ser Ala Leu Cys Gly Pro Glu Gly Tyr Pro His Leu
            20                  25                  30

Ile Val Asp Gly Arg Phe Thr His Ala Gly Asp Phe Leu Ile Pro Ser
        35                  40                  45

Ile Leu Phe Leu Tyr Ile Ala Gly Trp Ile Gly Trp Val Gly Arg Ser
    50                  55                  60
```

```
Tyr Leu Ile Glu Ile Arg Glu Ser Lys Asn Pro Glu Met Gln Glu Val
 65                  70                  75                  80

Val Ile Asn Val Pro Leu Ala Ile Lys Lys Met Leu Gly Gly Phe Leu
                 85                  90                  95

Trp Pro Leu Ala Ala Val Gly Glu Tyr Thr Ser Gly Lys Leu Val Met
            100                 105                 110

Lys Asp Ser Glu Ile Pro Thr Ser Pro Arg
        115                 120

<210> SEQ ID NO 15
<211> LENGTH: 558
<212> TYPE: PRT
<213> ORGANISM: Artificial sequence
<220> FEATURE:
<223> OTHER INFORMATION: 1HydFd :a recombinant product of pETDuet
      Hyd E + A Cr Fd with no linker

<400> SEQUENCE: 15

Met Gly Trp Ser His Pro Gln Phe Glu Lys Arg Ser Glu Asn Leu Tyr
  1               5                  10                  15

Phe Gln Gly Ala Ala Pro Ala Ala Glu Ala Pro Leu Ser His Val Gln
             20                  25                  30

Gln Ala Leu Ala Glu Leu Ala Lys Pro Lys Asp Asp Pro Thr Arg Lys
         35                  40                  45

His Val Cys Val Gln Val Ala Pro Ala Val Arg Val Ala Ile Ala Glu
     50                  55                  60

Thr Leu Gly Leu Ala Pro Gly Ala Thr Thr Pro Lys Gln Leu Ala Glu
 65                  70                  75                  80

Gly Leu Arg Arg Leu Gly Phe Asp Glu Val Phe Asp Thr Leu Phe Gly
                 85                  90                  95

Ala Asp Leu Thr Ile Met Glu Glu Gly Ser Glu Leu Leu His Arg Leu
            100                 105                 110

Thr Glu His Leu Glu Ala His Pro His Ser Asp Glu Pro Leu Pro Met
        115                 120                 125

Phe Thr Ser Cys Cys Pro Gly Trp Ile Ala Met Leu Glu Lys Ser Tyr
    130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
            180                 185                 190

Ser Glu Ala Asp Arg Asp Trp Phe Cys Val Asp Ala Asp Pro Thr Leu
        195                 200                 205

Arg Gln Leu Asp His Val Ile Thr Thr Val Glu Leu Gly Asn Ile Phe
    210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Glu Leu Phe Thr
            260                 265                 270

Gly Thr Pro Leu Pro Arg Leu Ser Leu Ser Glu Val Arg Gly Met Asp
        275                 280                 285

Gly Ile Lys Glu Thr Asn Ile Thr Met Val Pro Ala Pro Gly Ser Lys
    290                 295                 300
```

```
Phe Glu Glu Leu Leu Lys His Arg Ala Ala Arg Ala Glu Ala Ala
305                 310                 315                 320

Ala His Gly Thr Pro Gly Pro Leu Ala Trp Asp Gly Ala Gly Phe
            325                 330                 335

Thr Ser Glu Asp Gly Arg Gly Ile Thr Leu Arg Val Ala Val Ala
                340                 345                 350

Asn Gly Leu Gly Asn Ala Lys Lys Leu Ile Thr Lys Met Gln Ala Gly
        355                 360                 365

Glu Ala Lys Tyr Asp Phe Val Glu Ile Met Ala Cys Pro Ala Gly Cys
    370                 375                 380

Val Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
            405                 410                 415

Arg Ser His Glu Asn Pro Ser Ile Arg Glu Leu Tyr Asp Thr Tyr Leu
                420                 425                 430

Gly Glu Pro Leu Gly His Lys Ala His Glu Leu Leu His Thr His Tyr
        435                 440                 445

Val Ala Gly Gly Val Glu Glu Lys Asp Glu Lys Lys Met Ala Ser Tyr
    450                 455                 460

Thr Val Lys Leu Ile Thr Pro Asp Gly Glu Ser Ser Ile Glu Cys Ser
465                 470                 475                 480

Asp Asp Thr Tyr Ile Leu Asp Ala Ala Glu Glu Ala Gly Leu Asp Leu
            485                 490                 495

Pro Tyr Ser Cys Arg Ala Gly Ala Cys Ser Thr Cys Ala Gly Lys Ile
                500                 505                 510

Thr Ala Gly Ser Val Asp Gln Ser Asp Gln Ser Phe Leu Asp Asp
        515                 520                 525

Gln Ile Glu Ala Gly Tyr Val Leu Thr Cys Val Ala Tyr Pro Thr Ser
    530                 535                 540

Asp Cys Thr Ile Glu Thr His Lys Glu Glu Leu Thr Ala
545                 550                 555

<210> SEQ ID NO 16
<211> LENGTH: 563
<212> TYPE: PRT
<213> ORGANISM: Artificial sequence
<220> FEATURE:
<223> OTHER INFORMATION: 2HydFd : a recombinant product of pETDuet
      Hyd E + A Cr Fd with a short linker

<400> SEQUENCE: 16

Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
            20                  25                  30

Gln Ala Leu Ala Glu Leu Ala Lys Pro Lys Asp Asp Pro Thr Arg Lys
        35                  40                  45

His Val Cys Val Gln Val Ala Pro Ala Val Arg Val Ala Ile Ala Glu
    50                  55                  60

Thr Leu Gly Leu Ala Pro Gly Ala Thr Thr Pro Lys Gln Leu Ala Glu
65                  70                  75                  80

Gly Leu Arg Arg Leu Gly Phe Asp Glu Val Phe Asp Thr Leu Phe Gly
            85                  90                  95

Ala Asp Leu Thr Ile Met Glu Glu Gly Ser Glu Leu Leu His Arg Leu
        100                 105                 110
```

```
Thr Glu His Leu Glu Ala His Pro His Ser Asp Glu Pro Leu Pro Met
        115                 120                 125

Phe Thr Ser Cys Cys Pro Gly Trp Ile Ala Met Leu Glu Lys Ser Tyr
    130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
                180                 185                 190

Ser Glu Ala Asp Arg Asp Trp Phe Cys Val Asp Ala Asp Pro Thr Leu
            195                 200                 205

Arg Gln Leu Asp His Val Ile Thr Thr Val Glu Leu Gly Asn Ile Phe
        210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Glu Leu Phe Thr
            260                 265                 270

Gly Thr Pro Leu Pro Arg Leu Ser Leu Ser Glu Val Arg Gly Met Asp
        275                 280                 285

Gly Ile Lys Glu Thr Asn Ile Thr Met Val Pro Ala Pro Gly Ser Lys
    290                 295                 300

Phe Glu Glu Leu Leu Lys His Arg Ala Ala Ala Arg Ala Glu Ala Ala
305                 310                 315                 320

Ala His Gly Thr Pro Gly Pro Leu Ala Trp Asp Gly Gly Ala Gly Phe
                325                 330                 335

Thr Ser Glu Asp Gly Arg Gly Gly Ile Thr Leu Arg Val Ala Val Ala
            340                 345                 350

Asn Gly Leu Gly Asn Ala Lys Lys Leu Ile Thr Lys Met Gln Ala Gly
        355                 360                 365

Glu Ala Lys Tyr Asp Phe Val Glu Ile Met Ala Cys Pro Ala Gly Cys
    370                 375                 380

Val Gly Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
                405                 410                 415

Arg Ser His Glu Asn Pro Ser Ile Arg Glu Leu Tyr Asp Thr Tyr Leu
            420                 425                 430

Gly Glu Pro Leu Gly His Lys Ala His Glu Leu Leu His Thr His Tyr
        435                 440                 445

Val Ala Gly Gly Val Glu Glu Lys Asp Glu Lys Lys Gly Gly Gly Gly
    450                 455                 460

Ser Met Ala Ser Tyr Thr Val Lys Leu Ile Thr Pro Asp Gly Glu Ser
465                 470                 475                 480

Ser Ile Glu Cys Ser Asp Asp Thr Tyr Ile Leu Asp Ala Ala Glu Glu
                485                 490                 495

Ala Gly Leu Asp Leu Pro Tyr Ser Cys Arg Ala Gly Ala Cys Ser Thr
            500                 505                 510

Cys Ala Gly Lys Ile Thr Ala Gly Ser Val Asp Gln Ser Asp Gln Ser
        515                 520                 525

Phe Leu Asp Asp Asp Gln Ile Glu Ala Gly Tyr Val Leu Thr Cys Val
```

```
                530               535                540
Ala Tyr Pro Thr Ser Asp Cys Thr Ile Glu Thr His Lys Glu Glu
545                 550               555                560

Leu Thr Ala

<210> SEQ ID NO 17
<211> LENGTH: 568
<212> TYPE: PRT
<213> ORGANISM: Artificial sequence
<220> FEATURE:
<223> OTHER INFORMATION: 3HydFd : a recombinant product of pETDuet
      Hyd E + A Cr Fd with a medium linker

<400> SEQUENCE: 17

Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
                20                  25                  30

Gln Ala Leu Ala Glu Leu Ala Lys Pro Lys Asp Asp Pro Thr Arg Lys
            35                  40                  45

His Val Cys Val Gln Val Ala Pro Ala Val Arg Val Ala Ile Ala Glu
50                  55                  60

Thr Leu Gly Leu Ala Pro Gly Ala Thr Thr Pro Lys Gln Leu Ala Glu
65                  70                  75                  80

Gly Leu Arg Arg Leu Gly Phe Asp Glu Val Phe Asp Thr Leu Phe Gly
                85                  90                  95

Ala Asp Leu Thr Ile Met Glu Glu Gly Ser Glu Leu Leu His Arg Leu
            100                 105                 110

Thr Glu His Leu Glu Ala His Pro His Ser Asp Glu Pro Leu Pro Met
        115                 120                 125

Phe Thr Ser Cys Cys Pro Gly Trp Ile Ala Met Leu Glu Lys Ser Tyr
    130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
            180                 185                 190

Ser Glu Ala Asp Arg Asp Trp Phe Cys Val Asp Ala Asp Pro Thr Leu
        195                 200                 205

Arg Gln Leu Asp His Val Ile Thr Thr Val Glu Leu Gly Asn Ile Phe
    210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Glu Leu Phe Thr
            260                 265                 270

Gly Thr Pro Leu Pro Arg Leu Ser Leu Ser Glu Val Arg Gly Met Asp
        275                 280                 285

Gly Ile Lys Glu Thr Asn Ile Thr Met Val Pro Ala Pro Gly Ser Lys
    290                 295                 300

Phe Glu Glu Leu Leu Lys His Arg Ala Ala Arg Ala Glu Ala Ala
305                 310                 315                 320

Ala His Gly Thr Pro Gly Pro Leu Ala Trp Asp Gly Gly Ala Gly Phe
                325                 330                 335
```

```
Thr Ser Glu Asp Gly Arg Gly Ile Thr Leu Arg Val Ala Val Ala
            340                 345                 350

Asn Gly Leu Gly Asn Ala Lys Lys Leu Ile Thr Lys Met Gln Ala Gly
            355                 360                 365

Glu Ala Lys Tyr Asp Phe Val Glu Ile Met Ala Cys Pro Ala Gly Cys
370                 375                 380

Val Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
                405                 410                 415

Arg Ser His Glu Asn Pro Ser Ile Arg Glu Leu Tyr Asp Thr Tyr Leu
                420                 425                 430

Gly Glu Pro Leu Gly His Lys Ala His Glu Leu Leu His Thr His Tyr
            435                 440                 445

Val Ala Gly Gly Val Glu Glu Lys Asp Glu Lys Lys Gly Gly Gly Gly
450                 455                 460

Ser Gly Gly Gly Gly Ser Met Ala Ser Tyr Thr Val Lys Leu Ile Thr
465                 470                 475                 480

Pro Asp Gly Glu Ser Ser Ile Glu Cys Ser Asp Asp Thr Tyr Ile Leu
                485                 490                 495

Asp Ala Ala Glu Glu Ala Gly Leu Asp Leu Pro Tyr Ser Cys Arg Ala
                500                 505                 510

Gly Ala Cys Ser Thr Cys Ala Gly Lys Ile Thr Ala Gly Ser Val Asp
                515                 520                 525

Gln Ser Asp Gln Ser Phe Leu Asp Asp Gln Ile Glu Ala Gly Tyr
            530                 535                 540

Val Leu Thr Cys Val Ala Tyr Pro Thr Ser Asp Cys Thr Ile Glu Thr
545                 550                 555                 560

His Lys Glu Glu Glu Leu Thr Ala
                565

<210> SEQ ID NO 18
<211> LENGTH: 527
<212> TYPE: PRT
<213> ORGANISM: Artificial sequence
<220> FEATURE:
<223> OTHER INFORMATION: 4HydFd : a recombinant product of Hyd E + A Cr
      C' truncated Fd N' truncated and with no linker

<400> SEQUENCE: 18

Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
                20                  25                  30

Gln Ala Leu Ala Glu Leu Ala Lys Pro Lys Asp Asp Pro Thr Arg Lys
            35                  40                  45

His Val Cys Val Gln Val Ala Pro Ala Val Arg Val Ala Ile Ala Glu
        50                  55                  60

Thr Leu Gly Leu Ala Pro Gly Ala Thr Thr Pro Lys Gln Leu Ala Glu
65                  70                  75                  80

Gly Leu Arg Arg Leu Gly Phe Asp Glu Val Phe Asp Thr Leu Phe Gly
                85                  90                  95

Ala Asp Leu Thr Ile Met Glu Glu Gly Ser Glu Leu Leu His Arg Leu
                100                 105                 110

Thr Glu His Leu Glu Ala His Pro His Ser Asp Glu Pro Leu Pro Met
            115                 120                 125
```

Phe Thr Ser Cys Cys Pro Gly Trp Ile Ala Met Leu Glu Lys Ser Tyr
130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
            180                 185                 190

Ser Glu Ala Asp Arg Asp Trp Phe Cys Val Asp Ala Asp Pro Thr Leu
        195                 200                 205

Arg Gln Leu Asp His Val Ile Thr Val Glu Leu Gly Asn Ile Phe
210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Glu Leu Phe Thr
            260                 265                 270

Gly Thr Pro Leu Pro Arg Leu Ser Leu Ser Glu Val Arg Gly Met Asp
        275                 280                 285

Gly Ile Lys Glu Thr Asn Ile Thr Met Val Pro Ala Pro Gly Ser Lys
    290                 295                 300

Phe Glu Glu Leu Leu Lys His Arg Ala Ala Ala Arg Ala Glu Ala Ala
305                 310                 315                 320

Ala His Gly Thr Pro Gly Pro Leu Ala Trp Asp Gly Ala Gly Phe
                325                 330                 335

Thr Ser Glu Asp Gly Arg Gly Gly Ile Thr Leu Arg Val Ala Val Ala
            340                 345                 350

Asn Gly Leu Gly Asn Ala Lys Lys Leu Ile Thr Lys Met Gln Ala Gly
        355                 360                 365

Glu Ala Lys Tyr Asp Phe Val Glu Ile Met Ala Cys Pro Ala Gly Cys
    370                 375                 380

Val Gly Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
                405                 410                 415

Arg Ser His Glu Asn Pro Ser Ile Arg Glu Leu Tyr Asp Thr Tyr Leu
            420                 425                 430

Gly Glu Pro Leu Gly His Lys Ala His Glu Leu Leu His Thr His Tyr
        435                 440                 445

Val Asp Asp Thr Tyr Ile Leu Asp Ala Ala Glu Ala Gly Leu Asp
    450                 455                 460

Leu Pro Tyr Ser Cys Arg Ala Gly Ala Cys Ser Thr Cys Ala Gly Lys
465                 470                 475                 480

Ile Thr Ala Gly Ser Val Asp Gln Ser Asp Gln Ser Phe Leu Asp Asp
                485                 490                 495

Asp Gln Ile Glu Ala Gly Tyr Val Leu Thr Cys Val Ala Tyr Pro Thr
            500                 505                 510

Ser Asp Cys Thr Ile Glu Thr His Lys Glu Glu Leu Thr Ala
        515                 520                 525

<210> SEQ ID NO 19
<211> LENGTH: 547
<212> TYPE: PRT

<213> ORGANISM: Artificial sequence
<220> FEATURE:
<223> OTHER INFORMATION: 5HydFd : a recombinant product of pETDuet Hyd E + A Cr C' truncated Fd and with no linker

<400> SEQUENCE: 19

```
Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
                20                  25                  30

Gln Ala Leu Ala Glu Leu Ala Lys Pro Lys Asp Asp Pro Thr Arg Lys
            35                  40                  45

His Val Cys Val Gln Val Ala Pro Ala Val Arg Val Ala Ile Ala Glu
        50                  55                  60

Thr Leu Gly Leu Ala Pro Gly Ala Thr Thr Pro Lys Gln Leu Ala Glu
65                  70                  75                  80

Gly Leu Arg Arg Leu Gly Phe Asp Glu Val Phe Asp Thr Leu Phe Gly
                85                  90                  95

Ala Asp Leu Thr Ile Met Glu Glu Gly Ser Glu Leu Leu His Arg Leu
                100                 105                 110

Thr Glu His Leu Glu Ala His Pro His Ser Asp Glu Pro Leu Pro Met
            115                 120                 125

Phe Thr Ser Cys Cys Pro Gly Trp Ile Ala Met Leu Glu Lys Ser Tyr
130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
                180                 185                 190

Ser Glu Ala Asp Arg Asp Trp Phe Cys Val Asp Ala Asp Pro Thr Leu
            195                 200                 205

Arg Gln Leu Asp His Val Ile Thr Thr Val Glu Leu Gly Asn Ile Phe
210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Glu Leu Phe Thr
                260                 265                 270

Gly Thr Pro Leu Pro Arg Leu Ser Leu Ser Glu Val Arg Gly Met Asp
            275                 280                 285

Gly Ile Lys Glu Thr Asn Ile Thr Met Val Pro Ala Pro Gly Ser Lys
290                 295                 300

Phe Glu Glu Leu Leu Lys His Arg Ala Ala Ala Arg Ala Glu Ala Ala
305                 310                 315                 320

Ala His Gly Thr Pro Gly Pro Leu Ala Trp Asp Gly Gly Ala Gly Phe
                325                 330                 335

Thr Ser Glu Asp Gly Arg Gly Ile Thr Leu Arg Val Ala Val Ala
                340                 345                 350

Asn Gly Leu Gly Asn Ala Lys Lys Leu Ile Thr Lys Met Gln Ala Gly
            355                 360                 365

Glu Ala Lys Tyr Asp Phe Val Glu Ile Met Ala Cys Pro Ala Gly Cys
370                 375                 380

Val Gly Gly Gly Gly Gln Pro Arg Ser Thr Asp Lys Ala Ile Thr Gln
```

```
                385                 390                 395                 400
Lys Arg Gln Ala Ala Leu Tyr Asn Leu Asp Glu Lys Ser Thr Leu Arg
                    405                 410                 415

Arg Ser His Glu Asn Pro Ser Ile Arg Glu Leu Tyr Asp Thr Tyr Leu
            420                 425                 430

Gly Glu Pro Leu Gly His Lys Ala His Glu Leu Leu His Thr His Tyr
        435                 440                 445

Val Met Ala Ser Tyr Thr Val Lys Leu Ile Thr Pro Asp Gly Glu Ser
    450                 455                 460

Ser Ile Glu Cys Ser Asp Asp Thr Tyr Ile Leu Asp Ala Ala Glu Glu
465                 470                 475                 480

Ala Gly Leu Asp Leu Pro Tyr Ser Cys Arg Ala Gly Ala Cys Ser Thr
                485                 490                 495

Cys Ala Gly Lys Ile Thr Ala Gly Ser Val Asp Gln Ser Asp Gln Ser
                    500                 505                 510

Phe Leu Asp Asp Gln Ile Glu Ala Gly Tyr Val Leu Thr Cys Val
                515                 520                 525

Ala Tyr Pro Thr Ser Asp Cys Thr Ile Glu Thr His Lys Glu Glu Glu
        530                 535                 540

Leu Thr Ala
545

<210> SEQ ID NO 20
<211> LENGTH: 538
<212> TYPE: PRT
<213> ORGANISM: Artificial sequence
<220> FEATURE:
<223> OTHER INFORMATION: 6HydFd : a recombinant product of pETDuet
      Hyd E + A Cr Fd N' truncated

<400> SEQUENCE: 20

Met Gly Trp Ser His Pro Gln Phe Glu Lys Arg Ser Glu Asn Leu Tyr
1               5                   10                  15

Phe Gln Gly Ala Ala Pro Ala Ala Glu Ala Pro Leu Ser His Val Gln
                20                  25                  30

Gln Ala Leu Ala Glu Leu Ala Lys Pro Lys Asp Asp Pro Thr Arg Lys
        35                  40                  45

His Val Cys Val Gln Val Ala Pro Ala Val Arg Val Ala Ile Ala Glu
    50                  55                  60

Thr Leu Gly Leu Ala Pro Gly Ala Thr Thr Pro Lys Gln Leu Ala Glu
65                  70                  75                  80

Gly Leu Arg Arg Leu Gly Phe Asp Glu Val Phe Asp Thr Leu Phe Gly
                85                  90                  95

Ala Asp Leu Thr Ile Met Glu Glu Gly Ser Glu Leu Leu His Arg Leu
                100                 105                 110

Thr Glu His Leu Glu Ala His Pro His Ser Asp Glu Pro Leu Pro Met
        115                 120                 125

Phe Thr Ser Cys Cys Pro Gly Trp Ile Ala Met Leu Glu Lys Ser Tyr
    130                 135                 140

Pro Asp Leu Ile Pro Tyr Val Ser Ser Cys Lys Ser Pro Gln Met Met
145                 150                 155                 160

Leu Ala Ala Met Val Lys Ser Tyr Leu Ala Glu Lys Lys Gly Ile Ala
                165                 170                 175

Pro Lys Asp Met Val Met Val Ser Ile Met Pro Cys Thr Arg Lys Gln
                180                 185                 190

Ser Glu Ala Asp Arg Asp Trp Phe Cys Val Asp Ala Asp Pro Thr Leu
```

Arg Gln Leu Asp His Val Ile Thr Thr Val Glu Leu Gly Asn Ile Phe
210                 215                 220

Lys Glu Arg Gly Ile Asn Leu Ala Glu Leu Pro Glu Gly Glu Trp Asp
225                 230                 235                 240

Asn Pro Met Gly Val Gly Ser Gly Ala Gly Val Leu Phe Gly Thr Thr
                245                 250                 255

Gly Gly Val Met Glu Ala Ala Leu Arg Thr Ala Tyr Glu Leu Phe Thr
                260                 265                 270

Gly Thr Pro Leu Pro Arg Leu Ser Leu Ser Glu Val Arg Gly Met Asp
            275                 280                 285

Gly Ile Lys Glu Thr Asn Ile Thr Met Val Pro Ala Pro Gly Ser Lys
        290                 295                 300

Phe Glu Glu Leu Leu Lys His Arg Ala Ala Arg Ala Glu Ala Ala
305                 310                 315                 320

Ala His Gly Thr Pro Gly Pro Leu Ala Trp Asp Gly Gly Ala Gly Phe
                325                 330                 335

Thr Ser Glu Asp Gly Arg Gly Gly Ile Thr Leu Arg Val Ala Val Ala
                340                 345                 350

Asn Gly Leu Gly Asn Ala Lys Lys Leu Ile Thr Lys Met Gln Ala Gly
            355                 360                 365

Glu Ala Lys Tyr Asp Phe Val Glu Ile Met Ala Cys Pro Ala Gly Cys
        370                 375                 380

Val Gly Gly Gly Gly Gln Pro Arg Ser Thr Asp Lys Ala Ile Thr Gln
385                 390                 395                 400

Lys Arg Gln Ala Ala Leu Tyr Asn Leu Asp Glu Lys Ser Thr Leu Arg
                405                 410                 415

Arg Ser His Glu Asn Pro Ser Ile Arg Glu Leu Tyr Asp Thr Tyr Leu
                420                 425                 430

Gly Glu Pro Leu Gly His Lys Ala His Glu Leu Leu His Thr His Tyr
            435                 440                 445

Val Ala Gly Gly Val Glu Glu Lys Asp Glu Lys Lys Asp Asp Thr Tyr
        450                 455                 460

Ile Leu Asp Ala Ala Glu Glu Ala Gly Leu Asp Leu Pro Tyr Ser Cys
465                 470                 475                 480

Arg Ala Gly Ala Cys Ser Thr Cys Ala Gly Lys Ile Thr Ala Gly Ser
                485                 490                 495

Val Asp Gln Ser Asp Gln Ser Phe Leu Asp Asp Asp Gln Ile Glu Ala
                500                 505                 510

Gly Tyr Val Leu Thr Cys Val Ala Tyr Pro Thr Ser Asp Cys Thr Ile
            515                 520                 525

Glu Thr His Lys Glu Glu Glu Leu Thr Ala
530                 535

<210> SEQ ID NO 21
<211> LENGTH: 1677
<212> TYPE: DNA
<213> ORGANISM: Artificial sequence
<220> FEATURE:
<223> OTHER INFORMATION: pETDuet Hyd E + A Cr Fd with no linker

<400> SEQUENCE: 21
atgggctgga gccatccgca gtttgaaaaa agatctgaaa acctgtattt tcagggcgct         60
gctcctgctg ctgaagcgcc gctgagccat gtgcagcagg cgctggcgga actggcgaaa       120
ccgaaagatg atccgacccg taagcatgtg tgcgtgcagg tggcgccggc ggtgcgtgtg       180

```
gcgatcgcgg aaaccctggg cctggcgccg ggcgcgacca ccccgaaaca gctggcggaa    240
ggcctgcgtc gtctgggctt tgatgaagtg ttcgataccc tgtttggcgc ggatctgacc    300
atcatggaag aaggcagcga actgctgcat cgtctgaccg aacatctgga agcgcatccg    360
catagcgatg aaccgctgcc gatgtttacc agctgctgcc cgggctggat tgcgatgctg    420
gaaaaaagct atccggatct gattccgtat gtgagcagct gcaaaagccc gcagatgatg    480
ctggcggcga tggtgaaaag ctatctggcg gaaaaaaag gcattgcgcc gaaagatatg    540
gtgatggtga gcattatgcc gtgcacccgt aaacagagcg aagcggatcg tgattggttc    600
tgcgtggatg cggatccgac cctgcgtcag ctggatcatg tgattaccac cgtggaactg    660
ggcaacattt ttaaagaacg tggcattaac ctggcggaaa ctgccggaagg cgaatgggat    720 aacccgatgg gcgtgggcag cggcgcgggc gtgctgttcg gcaccaccgg cggcgtgatg    780
gaagcggcgc tgcgtaccgc gtatgaactg tttaccggca ccccgctgcc gcgtctgagc    840
ctgagcgagg tgcgtggcat ggatggcatt aaagagacca acattaccat ggtgccggcg    900
ccgggcagca aatttgaaga actgctgaaa catcgtgcgg cggcgcgtgc ggaagcggcg    960
gcgcatggca ccccgggccc gctggcgtgg gatggcggcg cgggctttac cagcgaagat    1020
ggccgtggcg gcattaccct gcgtgtggcg gtggcgaacg gcctgggcaa cgcgaaaaaa    1080
ctgattacca aaatgcaggc gggcgaagcg aaatatgatt ttgtggaaat tatggcgtgc    1140
ccggcgggct gcgtgggcgg cggcgcccag ccgcgtagca ccgataaagc gatcacccag    1200
aaacgtcagg cggcgctgta aacctggat gagaagagca ccctgcgtcg tagccatgag    1260 aaccccgagca ttcgtgaact gtatgatacc tatctgggcg aaccgctggg ccataaagcg    1320
catgaactgc tgcataccca ttatgtgcg ggcggcgtgg aagaaaaaga tgaaaaaaaa    1380
atggcatcct ataccgttaa attgatcacc cccgatggtg aaagttccat cgaatgctct    1440
gacgataccc tatatcctcga tgctgcggaa gaagctggcc tagacctgcc ctattcctgc    1500
cgtgctgggg cttgctccac ctgtgccggt aagatcaccg ctggtagtgt tgaccaatcc    1560
gatcagtctt tcttggatga tgaccaaatt gaagctggtt atgttttgac ctgtgtagct    1620
tatcccacct ccgattgcac cattgaaacc cacaaagaag aagagctcac cgcataa      1677
```

<210> SEQ ID NO 22
<211> LENGTH: 1691
<212> TYPE: DNA
<213> ORGANISM: Artificial sequence
<220> FEATURE:
<223> OTHER INFORMATION: pETDuet Hyd E + A Cr Fd with a short linker

<400> SEQUENCE: 22

```
atgggctgga gccatccgca gtttgaaaaa agatctgaaa acctgtattt tcagggcgct     60
gctcctgctg ctgaagcgcc gctgagccat gtgcagcagg cgctggcgga actggcgaaa    120
ccgaaagatg atccgacccg taagcatgtt gcgtgcaggt ggcgccggcg gtgcgtgtgg    180
cgatcgcgga aaccctgggc ctggcgccgg gcgcgaccac ccccgaaacag ctggcggaag    240 gcctgcgtcg tctgggcttt gatgaagtgt tcgatacccct gtttggcgcg gatctgacca    300
tcatggaaga aggcagcgaa ctgctgcatc gtctgaccga acatctggaa gcgcatccgc    360
atagcgatga accgctgccg atgtttacca gctgctgccc gggctggatt gcgatgctgg    420
aaaaaagcta tccggatctg attccgtatg tgagcagctg caaaagcccg cagatgatgc    480
tggcggcgat ggtgaaaagc tatctggcgg aaaaaaaagg cattgcgccg aaagatatgg    540
tgatggtgag cattatgccg tgcacccgta aacagagcga agcggatcgt gattggttct    600
```

```
gcgtggatgc ggatccgacc ctgcgtcagc tggatcatgt gattaccacc gtggaactgg      660
gcaacatttt taaagaacgt ggcattaacc tggcggaact gccggaaggc gaatgggata      720
acccgatggg cgtgggcagc ggcgcgggcg tgctgttcgg caccaccggc ggcgtgatgg      780
aagcggcgct gcgtaccgcg tatgaactgt ttaccggcac cccgctgccg cgtctgagcc      840
tgagcgaggt gcgtggcatg gatggcatta agagaccaa cattaccatg gtgccggcgc       900
cgggcagcaa atttgaagaa ctgctgaaac atcgtgcggc ggcgcgtgcg gaagcggcgg      960
cgcatggcac cccgggcccg ctggcgtggg atggcgcgc gggctttacc agcgaagatg      1020
gccgtggcgg cattaccctg cgtgtggcgg tggcgaacgg cctgggcaac gcgaaaaaac     1080
tgattaccaa aatgcaggcg ggcgaagcga aatatgattt tgtggaaatt atggcgtgcc     1140
cggcgggctg cgtgggcggc ggcggccagc cgcgtagcac cgataaagcg atcacccaga     1200
aacgtcaggc ggcgctgtat aacctggatg agaagagcac cctgcgtcgt agccatgaga     1260
acccgagcat tcgtgaactg tatgatacct atctgggcga accgctgggc cataaagcgc     1320
atgaactgct gcatacccat tatgtggcgg gcggcgtgga agaaaaagat gaaaaaaaag     1380 gtggcggcg atccatggca tcctataccg ttaaattgat cacccccgat ggtgaaagtt      1440
ccatcgaatg ctctgacgat acctatatcc tcgatgctgc ggaagaagct ggcctagacc     1500
tgccctattc ctgccgtgct ggggcttgct ccacctgtgc cggtaagatc accgctggta     1560
gtgttgacca atccgatcag tctttcttgg atgatgacca aattgaagct ggttatgttt      1620
tgacctgtgt agcttatccc acctccgatt gcaccattga aacccacaaa gaagaagagc      1680
tcaccgcata a                                                           1691
```

<210> SEQ ID NO 23
<211> LENGTH: 1707
<212> TYPE: DNA
<213> ORGANISM: Artificial sequence
<220> FEATURE:
<223> OTHER INFORMATION: pETDuet Hyd E + A Cr Fd with a medium linker

<400> SEQUENCE: 23

```
atgggctgga gccatccgca gtttgaaaaa agatctgaaa acctgtattt tcagggcgct       60
gctcctgctg ctgaagcgcc gctgagccat gtgcagcagg cgctggcgga actggcgaaa     120
ccgaaagatg atccgacccg taagcatgtg tgcgtgcagg tggcgccggc ggtgcgtgtg     180
gcgatcgcgg aaaccctggg cctggcgccg ggcgcgacca ccccgaaaca gctggcggaa     240
ggcctgcgtc gtctgggctt tgatgaagtg ttcgataccc tgtttggcgc ggatctgacc     300
atcatggaag aaggcagcga actgctgcat cgtctgaccg aacatctgga agcgcatccg     360
catagcgatg aaccgctgcc gatgtttacc agctgctgcc cgggctggat tgcgatgctg     420
gaaaaaagct atccggatct gattccgtat gtgagcagct gcaaagccc gcagatgatg      480 ctggcggcga tggtgaaaag ctatctggcg aaaaaaaag gcattgcgcc gaaagatatg      540
gtgatggtga gcattatgcc gtgcacccgt aaacagagcg aagcggatcg tgattggttc      600
tgcgtggatg cggatccgac cctgcgtcag ctggatcatg tgattaccac cgtggaactg      660
ggcaacattt ttaaagaacg tggcattaac ctggcggaac tgccggaagg cgaatgggat      720
aacccgatgg gcgtgggcag cggcgcgggc gtgctgttcg gcaccaccgg cggcgtgatg      780
gaagcggcgc tgcgtaccgc gtatgaactg tttaccggca ccccgctgcc gcgtctgagc     840
ctgagcgagg tgcgtggcat ggatggcatt aagagaccac acattaccat ggtgccggcg     900
ccgggcagca aatttgaaga actgctgaaa catcgtgcgg cggcgcgtgc ggaagcggcg     960
```

```
gcgcatggca ccccgggccc gctggcgtgg gatggcggcg cgggctttac cagcgaagat    1020
ggccgtggcg gcattaccct gcgtgtggcg gtggcgaacg gcctgggcaa cgcgaaaaaa    1080
ctgattacca aaatgcaggc gggcgaagcg aaatatgatt ttgtggaaat tatggcgtgc    1140
ccggcgggct gcgtgggcgg cggcggccag ccgcgtagca ccgataaagc gatcacccag    1200
aaacgtcagg cggcgctgta taacctggat gagaagagca ccctgcgtcg tagccatgag    1260
aacccgagca ttcgtgaact gtatgatacc tatctgggcg aaccgctggg ccataaagcg    1320
catgaactgc tgcataccca ttatgtggcg ggcggcgtgg aagaaaaaga tgaaaaaaaa    1380
ggaggaggag gatccggcgg cggcggctcc atggcatcct ataccgttaa attgatcacc    1440
cccgatggtg aaagttccat cgaatgctct gacgatacct atatcctcga tgctgcggaa    1500
gaagctggcc tagacctgcc ctattcctgc cgtgctgggg cttgctccac ctgtgccggt    1560
aagatcaccg ctggtagtgt tgaccaatcc gatcagtctt tcttggatga tgaccaaatt    1620
gaagctggtt atgttttgac ctgtgtagct tatcccacct ccgattgcac cattgaaacc    1680
cacaaagaag aagagctcac cgcataa                                       1707
```

<210> SEQ ID NO 24
<211> LENGTH: 1584
<212> TYPE: DNA
<213> ORGANISM: Artificial sequence
<220> FEATURE:
<223> OTHER INFORMATION: pETDuet Hyd E + A Cr C' truncated Fd N'
      truncated and with no linker

<400> SEQUENCE: 24

```
atgggctgga gccatccgca gtttgaaaaa agatctgaaa acctgtattt tcagggcgct      60
gctcctgctg ctgaagcgcc gctgagccat gtgcagcagg cgctggcgga actggcgaaa     120
ccgaaagatg atccgacccg taagcatgtg tgcgtgcagg tggcgccggc ggtgcgtgtg     180
gcgatcgcgg aaaccctggg cctggcgccg ggcgcgacca ccccgaaaca gctggcggaa     240
ggcctgcgtc gtctgggctt tgatgaagtg ttcgataccc tgtttggcgc ggatctgacc     300
atcatggaag aaggcagcga actgctgcat cgtctgaccg aacatctgga agcgcatccg     360
catagcgatg aaccgctgcc gatgtttacc agctgctgcc cgggctggat tgcgatgctg     420
gaaaaaagct atccggatct gattccgtat gtgagcagct gcaaaagccc gcagatgatg     480
ctggcggcga tggtgaaaag ctatctggcg gaaaaaaaag gcattgcgcc gaaagatatg     540
gtgatggtga gcattatgcc gtgcacccgt aaacagagcg aagcggatcg tgattggttc     600
tgcgtggatg cggatccgac cctgcgtcag ctggatcatg tgattaccac cgtggaactg     660
ggcaacattt ttaaagaacg tggcattaac ctggcggaaa ctgccggaagg cgaatgggat     720 aacccgatgg gcgtgggcag cggcgcgggc gtgctgttcg caccaccgg cggcgtgatg     780 gaagcggcgc tgcgtaccgc gtatgaactg tttaccggca ccccgctgcc gcgtctgagc     840
ctgagcgagg tgcgtggcat ggatggcatt aaagagacca acattaccat ggtgccggcg     900
ccgggcagca aatttgaaga actgctgaaa catcgtgcgg cggcgcgtgc ggaagcggcg     960
gcgcatggca ccccgggccc gctggcgtgg gatggcggcg cgggctttac cagcgaagat    1020
ggccgtggcg gcattaccct gcgtgtggcg gtggcgaacg gcctgggcaa cgcgaaaaaa    1080
ctgattacca aaatgcaggc gggcgaagcg aaatatgatt ttgtggaaat tatggcgtgc    1140
ccggcgggct gcgtgggcgg cggcggccag ccgcgtagca ccgataaagc gatcacccag    1200
aaacgtcagg cggcgctgta taacctggat gagaagagca ccctgcgtcg tagccatgag    1260
```

-continued

| | |
|---|---|
| aacccgagca ttcgtgaact gtatgatacc tatctgggcg aaccgctggg ccataaagcg | 1320 |
| catgaactgc tgcataccca ttatgtggac gatacctata tcctcgatgc tgcggaagaa | 1380 |
| gctggcctag acctgcccta ttcctgccgt gctggggctt gctccacctg tgccggtaag | 1440 |
| atcaccgctg gtagtgttga ccaatccgat cagtctttct tggatgatga ccaaattgaa | 1500 |
| gctggttatg ttttgacctg tgtagcttat cccacctccg attgcaccat tgaaacccac | 1560 |
| aaagaagaag agctcaccgc ataa | 1584 |

<210> SEQ ID NO 25
<211> LENGTH: 1644
<212> TYPE: DNA
<213> ORGANISM: Artificial sequence
<220> FEATURE:
<223> OTHER INFORMATION: pETDuet Hyd E + A Cr C' truncated Fd with no linker

<400> SEQUENCE: 25

| | |
|---|---|
| atgggctgga gccatccgca gtttgaaaaa agatctgaaa acctgtattt tcagggcgct | 60 |
| gctcctgctg ctgaagcgcc gctgagccat gtgcagcagg cgctggcgga actggcgaaa | 120 |
| ccgaaagatg atccgacccg taagcatgtg tgcgtgcagg tggcgccggc ggtgcgtgtg | 180 |
| gcgatcgcgg aaaccctggg cctggcgccg ggcgcgacca ccccgaaaca gctggcggaa | 240 |
| ggcctgcgtc gtctgggctt tgatgaagtg ttcgataccc tgtttggcgc ggatctgacc | 300 |
| atcatggaag aaggcagcga actgctgcat cgtctgaccg aacatctgga agcgcatccg | 360 |
| catagcgatg aaccgctgcc gatgtttacc agctgctgcc cgggctggat tgcgatgctg | 420 |
| gaaaaaagct atccggatct gattccgtat gtgagcagct gcaaaagccc gcagatgatg | 480 |
| ctggcggcga tggtgaaaag ctatctggcg gaaaaaaaag cattgcgcc gaaagatatg | 540 |
| gtgatggtga gcattatgcc gtgcacccgt aaacagagcg aagcggatcg tgattggttc | 600 |
| tgcgtggatg cggatccgac cctgcgtcag ctggatcatg tgattaccac cgtgaactg | 660 |
| ggcaacattt ttaaagaacg tggcattaac ctggcggaac tgccggaagg cgaatgggat | 720 |
| aacccgatgg gcgtgggcag cggcgcgggc gtgctgttcg caccaccgg cggcgtgatg | 780 |
| gaagcggcgc tgcgtaccgc gtatgaactg tttaccggca ccccgctgcc gcgtctgagc | 840 |
| ctgagcgagg tgcgtggcat ggatggcatt aaagagacca acattaccat ggtgccggcg | 900 |
| ccgggcagca aatttgaaga actgctgaaa catcgtgcgg cggcgcgtgc ggaagcggcg | 960 |
| gcgcatggca ccccgggccc gctggcgtgg gatggcggcg cgggctttac cagcgaagat | 1020 |
| ggccgtggcg gcattaccct gcgtgtggcg gtggcgaacg gcctgggcaa cgcgaaaaaa | 1080 |
| ctgattacca aaatgcaggc gggcgaagcg aaatatgatt ttgtggaaat tatgcgcgtgc | 1140 |
| ccggcgggct gcgtgggcgg cggcggccag ccgcgtagca ccgataaagc gatcacccag | 1200 |
| aaacgtcagg cggcgctgta acctggat gagaagagca ccctgcgtcg tagccatgag | 1260 |
| aacccgagca ttcgtgaact gtatgatacc tatctgggcg aaccgctggg ccataaagcg | 1320 |
| catgaactgc tgcataccca ttatgtgatg gcatcctata ccgttaaatt gatcaccccc | 1380 |
| gatggtgaaa gttccatcga atgctctgac gatacctata tcctcgatgc tgcggaagaa | 1440 |
| gctggcctag acctgcccta ttcctgccgt gctggggctt gctccacctg tgccggtaag | 1500 |
| atcaccgctg gtagtgttga ccaatccgat cagtctttct tggatgatga ccaaattgaa | 1560 |
| gctggttatg ttttgacctg tgtagcttat cccacctccg attgcaccat tgaaacccac | 1620 |
| aaagaagaag agctcaccgc ataa | 1644 |

-continued

```
<210> SEQ ID NO 26
<211> LENGTH: 1617
<212> TYPE: DNA
<213> ORGANISM: Artificial sequence
<220> FEATURE:
<223> OTHER INFORMATION: pETDuet Hyd E + A Cr Fd N' truncated

<400> SEQUENCE: 26
atgggctgga gccatccgca gtttgaaaaa agatctgaaa acctgtatt  tcagggcgct      60
gctcctgctg ctgaagcgcc gctgagccat gtgcagcagg cgctggcgga actggcgaaa    120
ccgaaagatg atccgacccg taagcatgtg tgccgtgcagg tggcgccggc ggtgcgtgtg    180
gcgatcgcgg aaaccctggg cctggcgccg ggcgcgacca ccccgaaaca gctggcggaa    240
ggcctgcgtc gtctgggctt tgatgaagtg ttcgataccc tgtttggcgc ggatctgacc    300
atcatggaag aaggcagcga actgctgcat cgtctgaccg aacatctgga agcgcatccg    360
catagcgatg aaccgctgcc gatgtttacc agctgctgcc cgggctggat tgcgatgctg    420
gaaaaaagct atccggatct gattccgtat gtgagcagct gcaaaagccc gcagatgatg    480
ctggcggcga tggtgaaaag ctatctggcg gaaaaaaag gcattgcgcc gaaagatatg    540
gtgatggtga gcattatgcc gtgcacccgt aaacagagcg aagcggatcg tgattggttc    600
tgcgtggatg cggatccgac cctgcgtcag ctggatcatg tgattaccac cgtggaactg    660
ggcaacattt taaagaacg tggcattaac ctggcggaac tgccggaagg cgaatgggat    720
aacccgatgg gcgtgggcag cggcgcgggc gtgctgttcg gcaccaccgg cggcgtgatg    780
gaagcggcgc tgcgtaccgc gtatgaactg tttaccggca ccccgctgcc gcgtctgagc    840
ctgagcgagg tgcgtggcat ggatggcatt aaagagacca acattaccat ggtgccggcg    900
ccgggcagca aatttgaaga actgctgaaa catcgtgcgg cggcgcgtgc ggaagcggcg    960
gcgcatggca ccccgggccc gctggcgtgg gatggcggcg cgggctttac cagcgaagat   1020
ggccgtggcg gcattaccct gcgtgtggcg gtggcgaacg gcctgggcaa cgcgaaaaaa   1080
ctgattacca aaatgcaggc gggcgaagcg aaatatgatt ttgtggaaat tatggcgtgc   1140
ccggcgggct gcgtgggcgg cggcggccag ccgcgtagca ccgataaagc gatcacccag   1200
aaacgtcagg cggcgctgta taacctggat gagaagagca ccctgcgtcg tagccatgag   1260
aacccgagca ttcgtgaact gtatgatacc tatctgggcg aaccgctggg ccataaagcg   1320
catgaactgc tgcatacccca ttatgtggcg ggcggcgtgg aagaaaaaga tgaaaaaaaa   1380
gacgatacct atatcctcga tgctgcggaa gaagctggcc tagacctgcc ctattcctgc   1440
cgtgctgggg cttgctccac ctgtgccggt aagatcaccg ctggtagtgt tgaccaatcc   1500
gatcagtctt tcttggatga tgaccaaatt gaagctggtt atgttttgac ctgtgtagct   1560
tatcccacct ccgattgcac cattgaaacc cacaaagaag aagagctcac cgcataa     1617
```

PHOTOCATALYTIC HYDROGEN PRODUCTION IN CYANOBACTERIA

RELATED APPLICATIONS

This application is a division of U.S. patent application Ser. No. 13/322,171 filed on Dec. 20, 2011, which is a National Phase of PCT Patent Application No. PCT/IL2010/000419 filed on May 26, 2010, which claims the benefit of priority under 35 USC §119(e) of U.S. Provisional Patent Application No. 61/213,289 filed on May 26, 2009. The contents of the above applications are all incorporated by reference as if fully set forth herein in their entirety.

SEQUENCE LISTING STATEMENT

The ASCII file, entitled 57068SequenceListing.txt, created on Aug. 4, 2013, comprising 53,490 bytes, submitted concurrently with the filing of this application is incorporated herein by reference.

FIELD AND BACKGROUND OF THE INVENTION

The present invention relates to the generation of hydrogen in cyanobacteria and isolated polynucleotides for same.

The development of a clean, sustainable and economically viable energy supply for the future is one of the most urgent challenges of our generation. Oil production is expected to peak in the near future and economically viable oil reserves are expected to be largely depleted by 2050. A viable hydrogen economy requires clean, sustainable and economic ways of generating hydrogen. Current hydrogen production depends almost entirely on the use of non-renewable resources (i.e. steam reformation of natural gas, coal gasification and nuclear power driven electrolysis of water). Although these approaches are initially likely to drive a transition towards a hydrogen economy, the hydrogen produced is more expensive and contains less energy than the non-renewable energy source from which it is derived. In addition, the use of fossil fuels and nuclear power is unsustainable. Therefore, there is a clear need to establish economically viable means of hydrogen production.

A particularly desirable option is the production of hydrogen using photosynthetic machinery, since the ultimate energy source is solar energy. The twin hearts of the photosynthetic machinery in plants, algae, and cyanobacteria are the two photochemical reaction centers known as Photosystem I (PSI) and Photosystem II (PSII). PSII drives the most highly oxidizing reaction known to occur in biology, splitting water into oxygen, protons and electrons. Oxygen is released into the atmosphere and is responsible for maintaining aerobic life on Earth. The derived electrons are passed along the photosynthetic electron transport chain from PSII via Plastoquinone (PQ) to Cytochrome $b_{6f}$ (cyt $b_{6f}$) and Photosystem I (PSI). From PSI, most of the negative redox potential is stabilized in the form of reduced ferredoxin (Fd) that serves as an electron donor to ferredoxin-NADP$^+$-reductase (FNR) enzyme. Under normal physiological conditions, Fd reduces NADP$^+$ to NADPH via the Fd-FNR complex. In a parallel process (photophosphorylation), H$^+$ are released into the thylakoid lumen where they generate a H$^+$ gradient that is used to drive ATP production via ATP synthase. NADPH and ATP are subsequently used to produce starch and other forms of energy storage biomass.

Some green algae and cyanobacteria have evolved the ability to channel the protons and electrons stored in starch into hydrogen production under anaerobic conditions by expressing a hydrogenase enzyme. [Wunschiers, Stangier et al. 2001, Curr Microbiol 42(5): 353-60; Happe and Kaminski 2002, Eur J Biochem 269(3): 1022-32]. The hydrogenase enzyme is localized in the chloroplast stroma and obtains electrons from ferredoxin or flavodoxin that is reduced by Photosystem I and thus competes with FNR for the PSI generated electrons. However, oxygen is a powerful inhibitor of the hydrogenase enzyme and thus, the generation of hydrogen in these organisms is only transient. The most important challenge in photosynthetic hydrogen production is its spatial and/or temporal separation from oxygen production.

Efforts to generate oxygen-tolerant algal hydrogenases have not met with much success [Seibert et al. 2001, Strategies for improving oxygen tolerance of algal hydrogen production. Biohydrogen II. J. M. Miyake, T.; San Pietro, A., eds, Oxford, UK: Pergamon 67-77]. McTavish et al [J Bacteriol 177(14): 3960-4, 1995] have shown that site-directed mutagenesis of *Azotobacter vinelandii* hydrogenase can render hydrogen production insensitive to oxygen inhibition, but with a substantial (78%) loss of hydrogen evolution activity.

Plant and algal chloroplasts and cyanobacterial photosynthetic membranes contain two photosystems: PSII mediates the transfer of electrons from water (the initial electron donor) to the plastoquinone pool and PSI mediates electron transfer from plastocyanin to ferredoxin, thereby generating reducing power needed for $CO_2$ fixation in the form of NADPH. While PSII is known to be sensitive to photodamage, PSI is considered to be more stable than PSII. Therefore, it is conceivable that preventing the assembly of PSII should result in its rapid inactivation under sunlight, and cessation of water splitting (and oxygen generation). Melis (U.S. Patent Application No. 2001/005343) teaches a process in which the inhibition of hydrogenase activity was lifted by temporally separating the oxygen generating water splitting reaction, catalyzed by PSII, from the oxygen sensitive hydrogen production catalyzed by the chloroplast Hydrogenase (HydA). This separation was achieved by culturing green algae first in the presence of sulfur to build stores of an endogenous substrate and then in the absence of sulfur. The removal of sulfur results in the inactivation of Photosystem II so that cellular respiration leads to anaerobiosis, the induction of hydrogenase, and sustained hydrogen evolution in the light.

The Melis process is, however, subject to considerable practical constraints. The actual rate of hydrogen gas accumulation is at best 15 to 20% of the photosynthetic capacity of the cells [Melis and Happe 2001, Plant Physiol. November; 127(3):740-8] and suffers the inherent limitation that hydrogen production by sulfur deprivation of the algae cannot be continued indefinitely. The yield begins to level off and declines after about 40-70 hours of sulfur deprivation. After about 100 hours of sulfur deprivation the algae need to revert to a phase of normal photosynthesis to replenish endogenous substrates.

International Publication No. WO 03/067213 describes a process for hydrogen production using *Chlamydomonas reinhardtii* wherein the algae has been genetically modified to down regulate expression of a sulfate permease, CrcpSulP, through the insertion of an antisense sequence. This is said to render obsolete prior art sulfur deprivation techniques, as it obviates the need to physically remove sulfur nutrients from growth media in order to induce hydrogen production. The reduced sulfur uptake by the cell using this technique not only results in a substantial lowering of the levels of the major chloroplast proteins such as Rubisco, D1 and the LHCII, but also deprives the cell of sulfur for use in the biosynthesis of other proteins.

Ihara et al (Ihara, Nakamoto et al. 2006; Ihara, Nishihara et al. 2006) teach a fusion protein comprising membrane bound [NiFe] hydrogenase (from the β-proteobacterium *Ralstonia eutropha* H16) and the peripheral PSI subunit PsaE of the cyanobacterium *Thermosynechococcus elongatus* as a direct light-to-hydrogen conversion system. The isolated hydrogenase-PSI isolated complex displayed light-driven hydrogen production at a rate of [0.58 μmol $H_2$]/[mg chlorophyll] h in vitro. The inefficiency of this system is thought to be derived from the mismatched ability of the hydrogenase to accept electrons compared to the ability of PSI to donate electrons.

Peters et al [Science, 282, 4 Dec., 1998] teach the isolation of an Fe-only hydrogenase from *clostridium pasteurianum* which naturally comprises ferrodoxin-like structures. Although this hydrogenase is potentially capable of directly generating hydrogen under illuminated conditions, it is still inhibited by oxygen.

There is thus a widely recognized need for, and it would be highly advantageous to have, a sustainable and efficient process for photosynthetic hydrogen production devoid of the above limitations.

SUMMARY OF THE INVENTION

According to an aspect of some embodiments of the present invention there is provided a cyanobacterial cell comprising a PSI complex which accepts electrons from at least one respiratory cytochrome.

According to an aspect of some embodiments of the present invention there is provided an isolated polynucleotide encoding a polypeptide which comprises a Photosystem I reaction centre subunit IX (PsaJ) amino acid sequence attached to a Photosystem I reaction centre subunit III precursor (PsaF) amino acid sequence which when expressed in a cyanobacteria accepts electrons from at least one respiratory cytochrome.

According to an aspect of some embodiments of the present invention there is provided a nucleic acid construct comprising the isolated polynucleotide of the present invention.

According to an aspect of some embodiments of the present invention there is provided a method of producing hydrogen gas, the method comprising culturing the cyanobacterial cell of the present invention under conditions that generate hydrogen gas in the cyanobacterial cell, thereby producing hydrogen gas.

According to an aspect of some embodiments of the present invention there is provided an isolated polypeptide as set forth in SEQ ID NO: 1.

According to an aspect of some embodiments of the present invention there is provided a bioreactor for producing hydrogen, comprising (i) a tubing for holding cells, wherein a first section of the tubing is placed in a first containment being maintained at a temperature of about 60-70° C. and a second section of the tubing is placed in a second containment being maintained at a temperature of about 30-50° C.; and (ii) a recirculation pump configured such that the cells circulate through the tubing.

According to some embodiments of the invention, the at least one respiratory cytochrome is cytochrome C or cytochrome M.

According to some embodiments of the invention, the cell is thermophilic.

According to some embodiments of the invention, the cell comprises a modified PsaJ polypeptide.

According to some embodiments of the invention, the modified PsaJ is attached to a PsaF.

According to some embodiments of the invention, the amino acid sequence of the polypeptide is set forth in SEQ ID NO: 1.

According to some embodiments of the invention, the PsaJ is attached to the PsaF by a linker.

According to some embodiments of the invention, the linker is a peptide bond.

According to some embodiments of the invention, the cell further comprises a polypeptide which comprises a hydrogenase enzyme attached to a heterologous ferrodoxin.

According to some embodiments of the invention, the hydrogenase enzyme is an algal Fe-only hydrogenase.

According to some embodiments of the invention, the heterologous ferrodoxin is a plant ferrodoxin.

According to some embodiments of the invention, the hydrogenase enzyme attached to a heterologous ferrodoxin has an amino acid sequence as set forth in SEQ ID NOs: 20-25.

According to some embodiments of the invention, the cell produces hydrogen at a temperature above about 55° C.

According to some embodiments of the invention, the cell is a *Mastigocladus laminosus* cell or a *Synechococcus elongates* cell.

According to some embodiments of the invention, the isolated polynucleotide encodes the polypeptide as set forth in SEQ ID NO: 1.

According to some embodiments of the invention, the isolated polynucleotide is as set forth in SEQ ID NO: 2 or SEQ ID NO: 6.

According to some embodiments of the invention, the nucleic acid construct further comprises a promoter.

According to some embodiments of the invention, the first containment is maintained under unaerobic conditions.

According to some embodiments of the invention, the second containment comprises organic matter.

According to some embodiments of the invention, the bioreactor comprises the cells of the present invention.

According to some embodiments of the invention, the first containment and the second containment are fabricated from a transparent material.

According to some embodiments of the invention, the first containment and the second containment are fabricated from an oxygen and hydrogen permeable plastic.

According to some embodiments of the invention, the method further comprises harvesting the hydrogen gas following the culturing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

This patent or application file contains at least one drawing executed in color. Copies of this patent or patent application publication with color drawing(s) will be provided by the Office upon request and payment of the necessary fee.

In the drawings:

FIGS. 1A-B are schematic diagrams illustrating the overall process of native light dependent hydrogen production in cyanobacteria FIG. 1A shows the overall membrane-associated process that is initiated by PSII (photosystem II). At the beginning water is being split to oxygen, protons and electrons by PSII. The generated electrons are transferred to the PQ (plastoquinone) pool from which most of the electrons are transferred to PSI. However, a small portion can be transferred to native cyanobacterial hydrogenase and some can also be respirated by complex IV. At PSI (photosystem I), the arriving electrons are recharged with photons energy. Next, charged electrons are transferred to Fd (ferredoxin) which shuttle them to FNR (Ferredoxin NADPH reductase) using the electrons and protons to produce NADPH. NADPH is a basic building block for the assimilation of carbon dioxide into sugars initially as glucose and finally in the higher form of glycogen. FIG. 1B shows a schematic view of cyanobacterial cell showing the intracellular membrane compartments in which the photosynthesis is taking place.

Figure 2A:
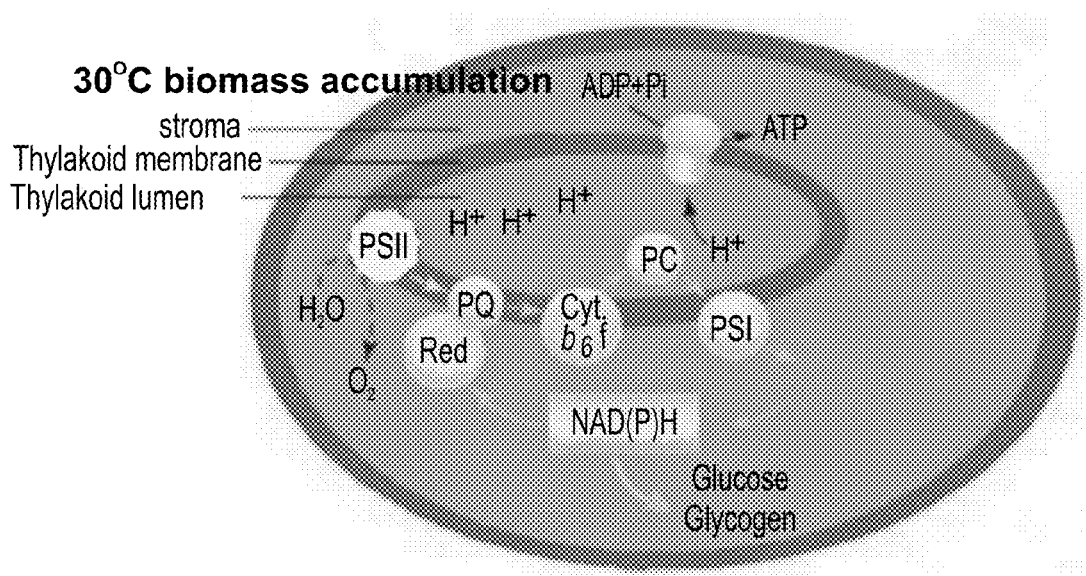
Figure 2B:
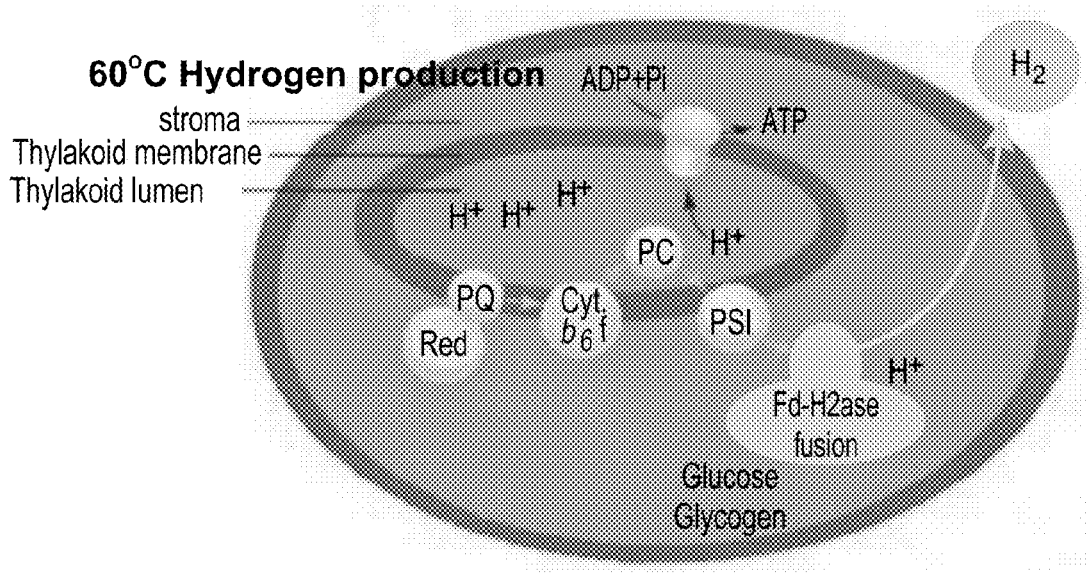

FIGS. 2A-B are schematic representation of a system for producing hydrogen according to an embodiment of the present invention. FIG. 2A: As long as the system is kept at low temperature (30-50° C.), natural photosynthetic process as described in FIG. 1 takes place. FIG. 2B: Transfer to a high temperature (60-70° C.), causes a thermo-sensitive PSII to stop working. This is accompanied by transformation of the cell into an anaerobic phase in which the Fd-hydrogenase chimera can be expressed. A combination of elevated electron transfer to PSI, as described herein and interference with Fd natural electron donating/accepting leads to an bypassed overall electron transport to Fd-hydrogenase chimera resulting in an overall elevation of hydrogen production.

Figure 3A:
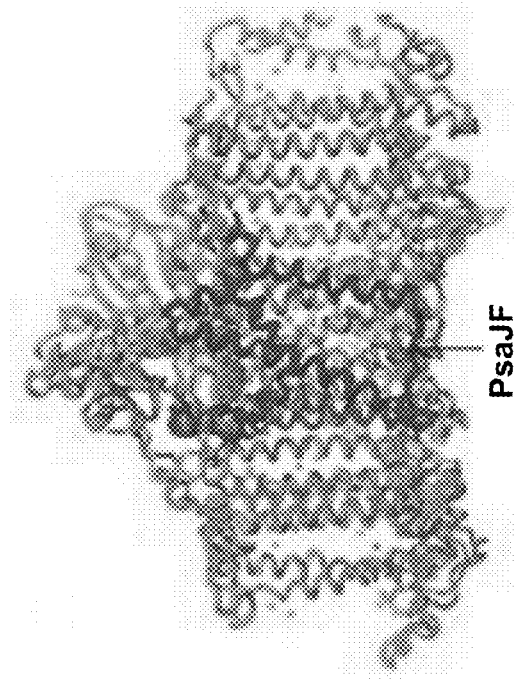
Figure 3B:
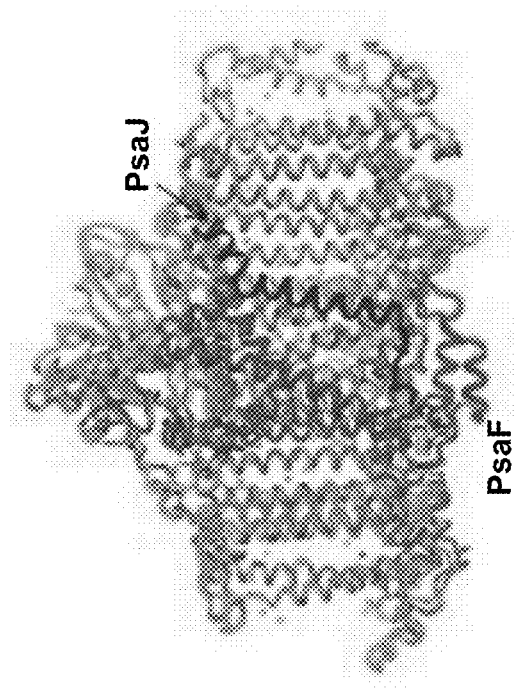
Figure 3C:
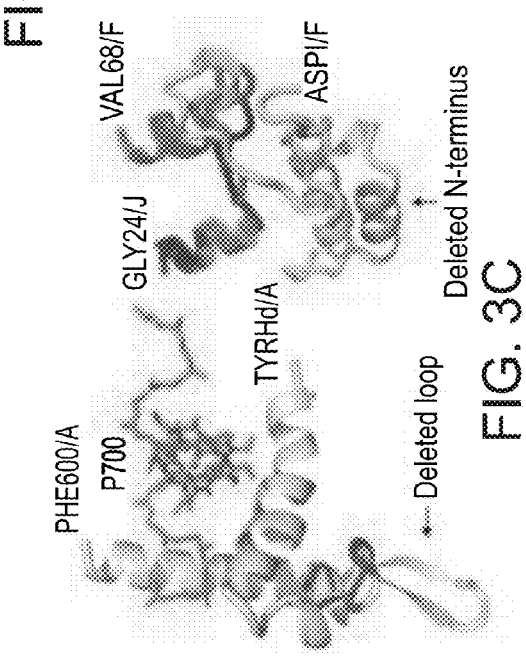

FIGS. 3A-C are models of the cyanobacteria and virus encoding PSI and structural consequences for the electron donor binding site. FIG. 3A: Cyanobacterial PSI composed of the subunits encoded by the viral operon. PsaF (magenta), PsaJ (blue). FIG. 3B: The viral PSI composed of the same subunits as in FIG. 3A except that PsaF and PsaJ were substituted by the PsaJF fusion protein (red). FIG. 3C: Superimposition of the two models showing the missing PsaF N-terminus and PsaA loop in the viral subunits in relation to P700. The viral short loop in PsaA is in red and the extended loop in the cyanobacterial PsaA is in gray. The viral PsaJF fusion protein is in magenta, cyanobacterial PsaJ in blue and PsaF in yellow.

Figure 4:
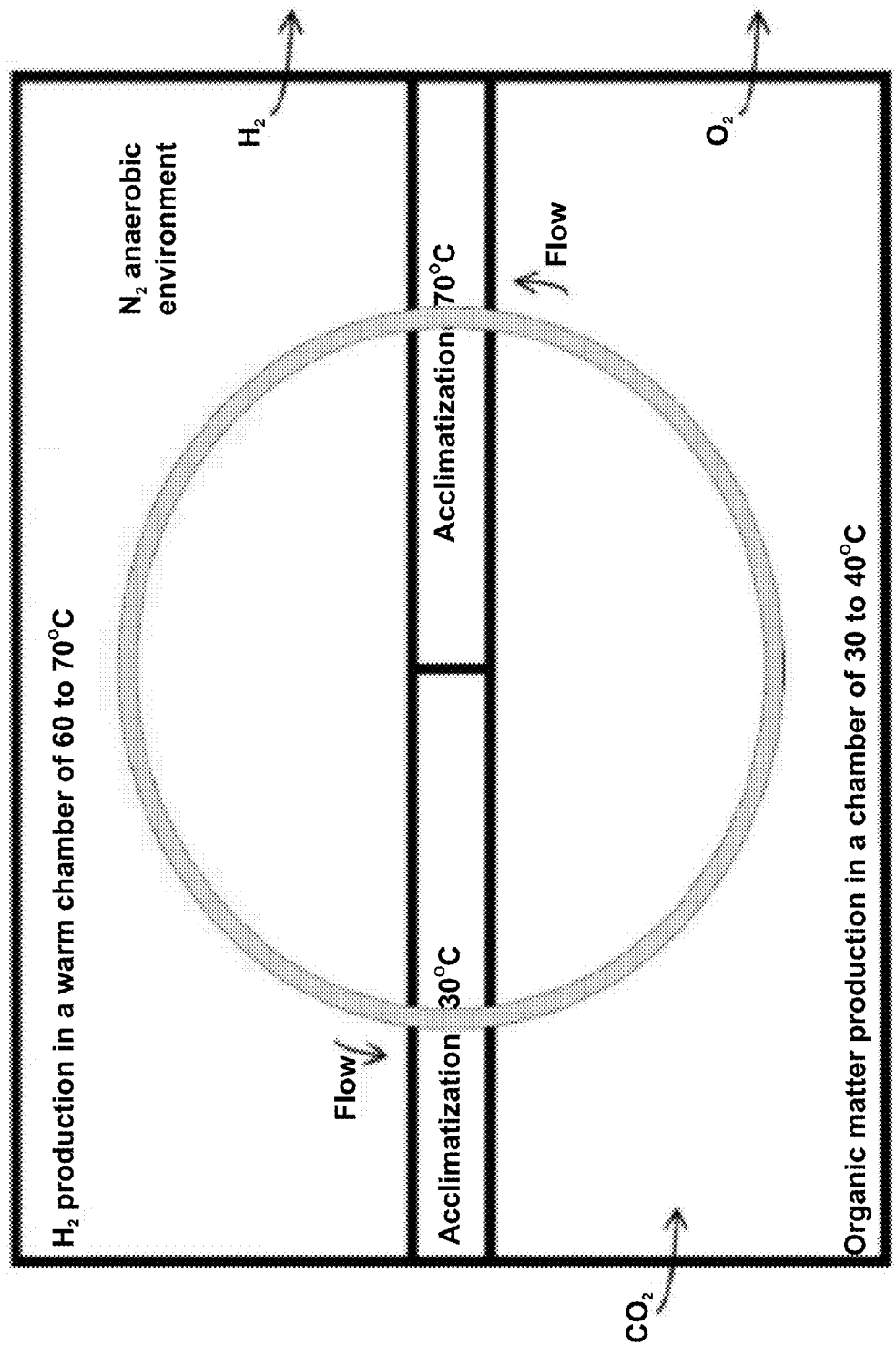

FIG. 4 is a schematic representation of the main elements of the hydrogen bioreactor according to an embodiment of the present invention. Several thousand circular tubes of about 2 mm diameter (one of them is shown in cyan) will be placed in an installation containing four chambers. The temperature-sensitive thermophilic cyanobacterial culture will circulate in the direction shown by the arrow. In the chamber with the permissive temperature of 30-50° C., the cyanobacteria will fix $CO_2$ into organic matter producing oxygen as a by-product. The flow will bring the culture into the acclimation chamber of 70° C. where PSII will be inactivated. From this point, the culture will move to the anaerobic chamber of 60-70° C. where the organic matter will be converted photosynthetically into hydrogen. Next, the flow will bring the culture into the 30-50° C. acclimatization chamber (optional) to reactivate PSII. Finally, it will be moved back to the organic matter production chamber. The flow rate of the various transparent chambers will be modified to maximize hydrogen production.

FIGS. 5A-C are schematic representations and photographs illustrating the expression and purification of a mutant PSI from *Synechocystis* sp. PCC 6803: FIG. 5A. A depiction of the native and mutant gene order in the *Synechocystis* genome. The JF fusion protein is under the control of the PsaF promoter (black box) and includes the entire PsaJ protein (40aa) and the last 121 amino acids from PsaF. The Kan resistance gene was used to select for transformation events, which were confirmed using PCR. FIG. 5B. Sucrose gradients of the native and mutant PSI showing that PSI exists in its trimeric form in the mutant strain. FIG. 5C. SDS PAGE of the wild type and mutant PSI subunit composition as they appear in the trimetric fractions collected from the sucrose gradient. The expected molecular weight of the fusion protein is 14 Kda.

Figure 6:
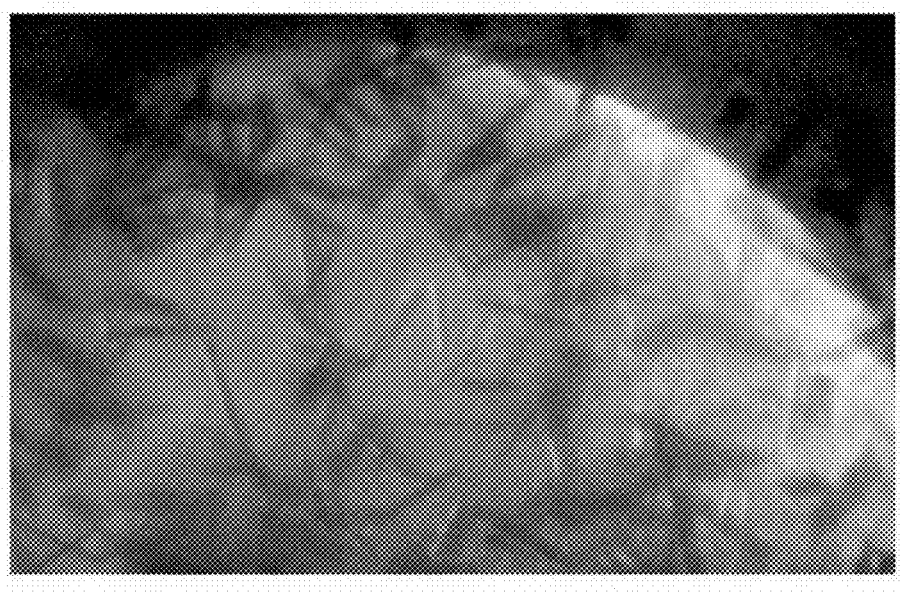

FIG. 6 is a photograph of the crystals of the mutant PsaJF PSI.

Figure 7:
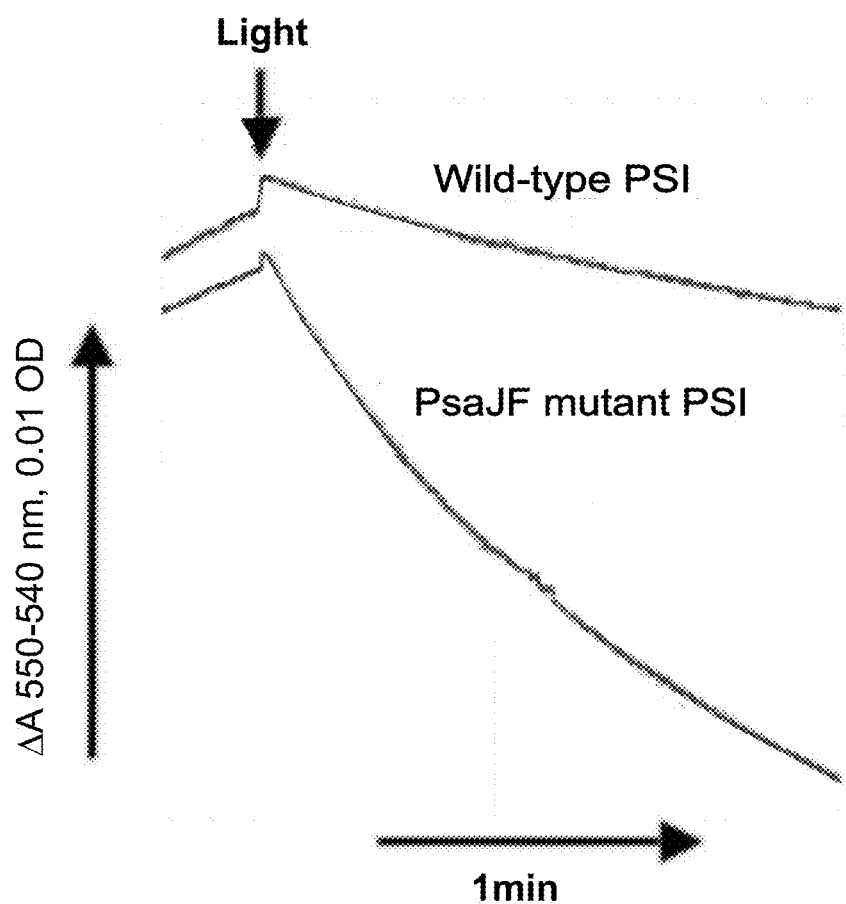

FIG. 7 is a graph illustrating faster oxidation kinetics of cytochrome c by a JF fusion containing PSI. Cytochrome c (horse heart) oxidation was followed using the absorbance difference between the 550 nm and 540 nm wavelengths in a dual wavelength spectrophotometer. The 1 ml solution consisted of 10 mM Bis-Tris pH7, wild-type PSI containing 40 µg chlorophyll or the JF-fusion mutant PSI containing 22 µg chlorophyll, 2 nmoles cytochrome c and 10 nmoles acrobat. Light-induced absorbance changes at 550-540 nm was recorded.

Figure 8:
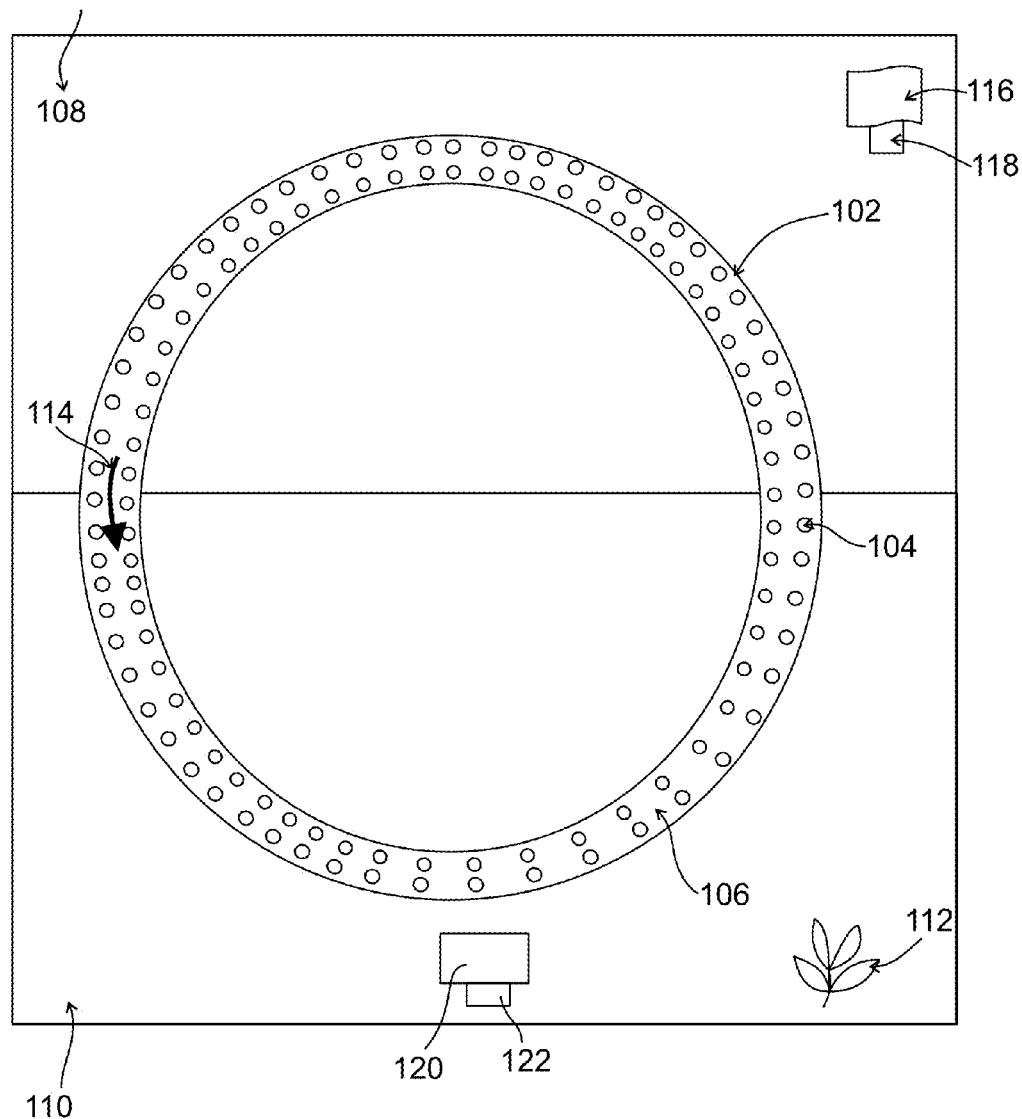

FIG. 8 is a schematic representation of a bioreactor according to an embodiment of the present invention.

Figure 9:
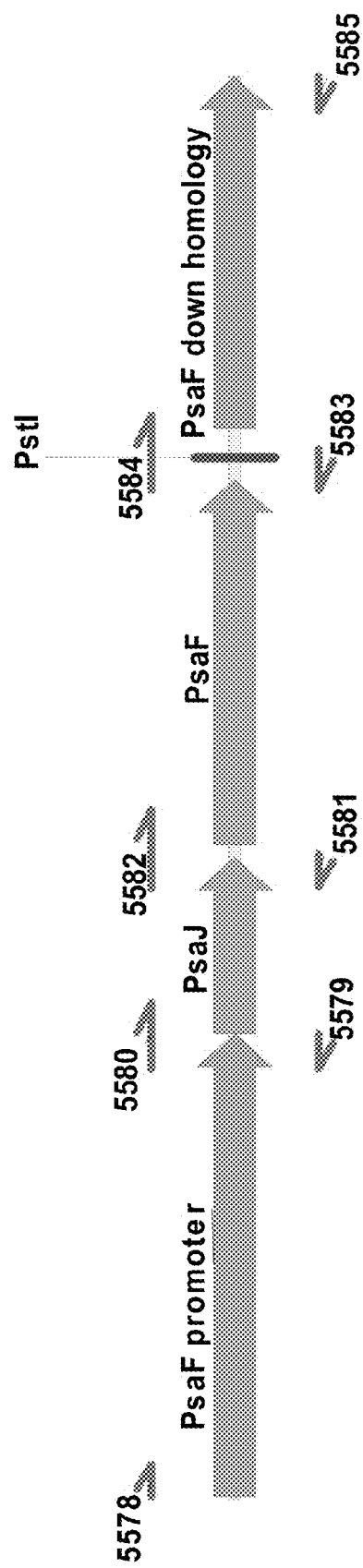

FIG. 9 is a schematic representation illustrating the expression of a mutant PSI from *Synechocystis* sp. PCC 6803.

DESCRIPTION OF THE PREFERRED EMBODIMENTS

The present invention relates to the generation of hydrogen in cyanobacteria and isolated polynucleotides for generating same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Molecular hydrogen is a candidate for replacing or supplementing fossil fuels as a source of clean energy. Natural biological production of hydrogen is based on the presence of hydrogenase enzymes present in certain green algae and photosynthetic bacteria which are capable of accepting electrons from photosystem I (PSI) and conversion thereof into hydrogen gas. The yield of molecular hydrogen from this process is limited for a number of reasons one of which being that PSI can only accept electrons from plastoquinone.

The present inventors postulated that the hydrogen yield could be increased if the photosynthetic organisms could be equipped with a PSI that has the potential to accept electrons from additional sources.

In a recent study, the potential structural consequences of assembling phage-encoded proteins into a cyanobacterial PSI complex were modeled in relation to the 2.5 Å structure of PSI from the cyanobacterium *Thermosynechococcus elongates*. The viral PsaJF fusion protein (where the C-terminus of PsaJ is fused to the N-terminus of PsaF) at the position 210 of subunit F of PSI, was modeled using the COOT program. The analysis showed that the viral PsaJF fusion protein fits perfectly at the position of subunits J and F in the PSI structure. The only prominent change that was observed was the absence of the N-terminus of subunit F, which is responsible for the specific binding of the natural electron donor (plastocyanin) of PSI (Nelson, N. & Yocum, C. Structure and function of photosystems I and II. Annu Rev Plant Biol 57, 521-565 (2006); Amunts, A., Drory, O. & Nelson, N. The structure of a plant photosystem I supercomplex at 3.4 Å resolution. Nature 447, 58-63 (2007). In chloroplasts of green algae and plants, this part of subunit F is elongated, resulting in higher affinity of plastocyanin to the chloroplast PSI (Hippler, M., Drepper, F., Farah, J. & Rochaix, J. D. Fast electron transfer from cytochrome c6 and plastocyanin to photosystem I of *Chlamydomonas reinhardtii* requires PsaF. Biochemistry 36, 6343-6349 (1997)). While both plastocyanin and cytochrome c6 are capable of donating electrons to PSI in *Chlamydomonas reinhardtii*, this site in higher plants is specific for plastocyanin. However, the electron donation to PSI in cyanobacteria is not at all promiscuous, and several soluble cytochromes, including the respiratory cytochrome c, fail to donate electrons to PSI (Kerfeld, C. A. & Krogmann, D. W. Photosynthetic cytochromes c in cyanobacteria, algae and plants. Annu Rev Plant Physiol Plant Mol Biol 49, 470 397-425 (1998).

The present inventors therefore suggest that the replacement of PsaJ and PsaF with the viral PsaJF fusion protein would enable electron donation through additional electron carriers, including cytochromes that usually function as electron donors to cytochrome oxidase.

The twin hearts of the photosynthetic machinery in plants, algae, and cyanobacteria are the two photochemical reaction centers known as Photosystem I (PSI) and Photosystem II (PSII). Since PSI can produce hydrogen and PSII produces oxygen, another important challenge in photosynthetic hydrogen production is its spatial and/or temporal separation from oxygen production. The present inventors propose a holistic solution to the above obstacle by using thermophilic cyanobacteria that are genetically engineered to separate the two systems for hydrogen production.

Accordingly, the present inventors propose further engineering of the cyanobacteria such that Photosystem II (PSII) will become temperature sensitive (i.e. not operate in the non-permissive temperature of 60° C., but will operate at permissive temperatures of about 50° C.).

Thus, in the non-permissive temperatures when PSII will be disabled (and oxygen production inhibited) the cytochromes will donate the electrons to PSI and hydrogen will be produced unhampered by the debilitating effects of oxygen on the hydrogenase. These periods will be alternated with the permissive temperature periods in which recovery of PSII will occur and regular growth and propagation of the cyanobacteria will proceed.

Thus, according to one aspect of the present invention there is provided a cyanobacterial cell comprising a PSI complex which accepts electrons from at least one respiratory cytochrome.

The term "cyanobacterial cell" refers to a bacterial cell that obtains its energy through photosynthesis.

According to one embodiment, the cyanobacteria is thermophilic—e.g. *Synechococcus elongatus* or *Mastigocladus laminosus*.

PSI is a protein-chlorophyll complex, present in green plants and cyanobacteria, that is part of the photosynthetic machinery within the thylakoid membrane. It is ellipsoidal in shape and has dimensions of about 9 by 15 nanometers. The PS I complex typically comprises chlorophyll molecules which serve as antennae which absorb photons and transfer the photon energy to P700, where this energy is captured and utilized to drive photochemical reactions. In addition to the P700 and the antenna chlorophylls, the PSI complex contains a number of electron acceptors. An electron released from P700 is transferred to a terminal acceptor at the reducing end of PSI through intermediate acceptors, and the electron is transported across the thylakoid membrane.

Typically PSI accepts electrons from specialized cytochrome or plastocyanin. The present invention contemplates modification of PSI such that it is able to accept electrons from additional sources such as respiratory cytochromes.

As used herein, the phrase "respiratory cytochromes" refers to soluble cytochromes of the respiratory electron transport chain, such as cytochrome c and cytochrome M (CytcM; Bernroitner M, et al., (2009) Biochim Biophys Acta. 1787, 135-143).

According to one embodiment, the PsaJ and PsaF subunits of PSI are modified to generate a PsaJF fusion subunit allowing PSI to become promiscuous and accept electrons from respiratory cytochrome donors whilst retaining the ability of PSI to donate the electrons to ferredoxin.

The term "PsaJ" refers to a subunit (IX) of the protein-chlorophyll complex photosystem I (PSI), present in green plants and cyanobacteria, that is part of the photosynthetic machinery within the thylakoid membrane.

Examples of PsaJ amino acid sequences are provided in Table 1 herein below.

TABLE 1

| Accession number | Protein name | Gene name | organism | length |
|---|---|---|---|---|
| NP_441427 (NC_000911.1) | PSI reaction centre subunit IX | psaJ | *Synechocystis* sp. PCC 6803 | 40 |
| B0LNU9 | PSI reaction centre subunit IX | psaJ | *Silene sordida* | 44 |
| B0LNS9 | PSI reaction centre subunit IX | psaJ | *Silene cryptoneura* | 44 |
| P0A429 | Photosystem I reaction center subunit IX | psaJ tsr2412 | *Thermosynechococcus elongatus* (strain BP-1) | 41 |
| B0LNI1 | PSI reaction centre subunit IX | psaJ | *Silene zawadskii* (Zawadskii's campion) | 44 |
| B0LP54 | PSI reaction centre subunit IX | psaJ | *Silene atocioides* | 44 |
| B0LND2 | PSI reaction centre subunit IX | psaJ | *Silene littorea* | 44 |

TABLE 1-continued

| Accession number | Protein name | Gene name | organism | length |
|---|---|---|---|---|
| B0LNJ2 | PSI reaction centre subunit IX | psaJ | *Silene sorensenis* | 44 |
| B0LNQ7 | PSI reaction centre subunit IX | psaJ | *Silene latifolia* (White campion) (Bladder campion) | 44 |
| B0LNE0 | PSI reaction centre subunit IX | psaJ | *Silene uniflora* | 44 |
| B0LP33 | PSI reaction centre subunit IX | psaJ | *Silene aegyptiaca* | 44 |
| B0LNZ4 | PSI reaction centre subunit IX | psaJ | *Silene pseudoatocion* | 44 |
| B0LN84 | PSI reaction centre subunit IX | psaJ | *Lychnis chalcedonica* (Scarlet lychnis) (Maltese cross) | 44 |
| B0LNX0 | PSI reaction centre subunit IX | psaJ | *Silene fruticosa* | 44 |
| B0LP12 | PSI reaction centre subunit IX | psaJ | *Silene schafta* | 42 |
| B0LNL5 | PSI reaction centre subunit IX | psaJ | *Silene integripetala* | 42 |
| B0LNP3 | PSI reaction centre subunit IX | psaJ | *Silene conica* (Striped corn catchfly) | 44 |
| B0LNA0 | PSI reaction centre subunit IX | psaJ | *Silene samia* | 44 |
| C3KEK5 | PSI reaction centre subunit IX | psaJ | *Ceratophyllum demersum* (Rigid hornwort) (Coontail) | 44 |

An exemplary PsaJ amino acid sequence is set forth in SEQ ID NO: 3.

The term "PsaF" refers to a subunit (III) of PSI. In its non-modified form PsaF is a plastocyanin-docking protein which contributes to the specific association of plastocyanin to PSI.

An exemplary PsaF amino acid sequence is set forth in SEQ ID NO: 4.

Examples of PsaF amino acid sequences are provided in Table 2 herein below.

TABLE 2

| Accession number | Protein name | Gene name | organism | length |
|---|---|---|---|---|
| P29256 | Photosystem I reaction center subunit III | psaF | *Synechocystis* sp. PCC 6803 | 165 |
| P0A401 | Photosystem I reaction center subunit III | psaF tlr2411 | *Thermosynechococcus elongatus* (strain BP-1) | 164 |

According to one embodiment, the PsaF subunit is modified (e.g. truncated) at the N terminus such that it reduces the affinity of plastocyanin to the chloroplast PSI. Contemplated truncations include removal of the first ten amino acids, more preferably the first 20 amino acids, more preferably the first 30 amino acids, more preferably the first 40 amino acids and even more preferably the first 43 amino acids. An exemplary amino acid sequence of a modified PsaF subunit is set forth in SEQ ID NO: 14.

According to a specific embodiment, the truncated PsaF subunit is attached to the PsaJ subunit to form a fusion protein in a similar fashion to the ones found in cyanophages.

The attachment may be via a linker peptide or directly.

Thus, the present invention contemplates cyanobacterial cells comprising PsaJF fusion proteins comprising an amino acid sequence at least 80% identical to that set forth in SEQ ID NO: 1.

A percent identity of a the fusion protein of this embodiment of the present invention to a polypeptide having an amino acid sequence set forth by SEQ ID NO: 1, may be determined in any of various ways. Preferably, the percent identity between polypeptides is determined using the Standard protein-protein BLAST [blastp] software of the NCBI.

The gene encoding the modified PsaJF proteins may be introduced into the cell and inserted by homologous recombination into PsaA or PsaB or any other location in the cyanobacterial genome. In order to do this, typically an additional one hundred base pairs are added on either side of the PsaJF coding region which are complementary to the cyanobacterial genome. Thus, for example a polynucleotide sequence as set forth by SEQ ID NO: 6 can be introduced into the cell such that it inserts into the cyanobacterial genome by homologous recombination. Alternatively or additionally, the native subunits such as PsaJ and PsaF may be engineered according to the virus (i.e. may be engineered to express a fusion protein) and substituted for the original subunits using recombinant techniques.

Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

To produce the polypeptides of the present invention using recombinant technology, a polynucleotide encoding the polypeptides of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

A contemplated promoter sequence which may be used in the nucleic acid constructs of the present invention is the PsaF promoter comprising a nucleic acid sequence as set forth in SEQ ID NO: 5.

Thus, the present invention contemplates isolated polynucleotides encoding the fusion protein of the present invention.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

An exemplary nucleic acid sequence of the polynucleotides of the present invention is set forth in SEQ ID NO: 2.

As mentioned hereinabove, polynucleotide sequences of the present invention are inserted into expression vectors (i.e., a nucleic acid construct) to enable expression of the recombinant polypeptide. The expression vector of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

A variety of prokaryotic or eukaryotic cells can be used as host-expression systems to express the polypeptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors or transformed with recombinant plasmid expression vectors, such as Ti plasmid, containing the polypeptide coding sequence.

According to one embodiment of this aspect of the present invention, the polynucleotides of the present invention are expressed directly in the cyanobacteria.

According to another embodiment of this aspect of the present invention, the polynucleotides of the present invention are expressed in heterologous cell systems.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide, this being particularly relevant when expressing in a heterologous system.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. In addition, cells of the current invention can be cultured under field conditions such as open ponds, covered ponds, plastic bags (see for example "A Look Back at the U.S. Department of Energy's Aquatic Species Program—Biodiesel from Algae, July 1998, U.S. Department of Energy's Office of Fuels Development, incorporated herein by reference). Such culturing conditions are within the expertise of one of ordinary skill in the art.

It will be appreciated that in order to study properties of the polypeptide it may be desired to isolate it (and optionally crystallize it). Thus, following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, salting out (as in ammonium sulfate precipitation), affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention may be retrieved in "substantially pure" form.

As used herein, the phrase "substantially pure" refers to a purity that allows for the effective use of the protein in the applications described herein.

The cyanobacterial cells of the present invention may be modified in additional ways in order to enhance hydrogen production.

Thus, according to one embodiment, the cyanobacterial cells are genetically modified to express a temperature sensitive photosystem II. In this way photosynthetic hydrogen production may be temporally separated from oxygen production. According to one embodiment, the Photosystem II (PSII) is modified such that it does not operate in the non-permissive temperature of about 60° C., but does operate at permissive temperatures of about 50° C.

Contemplated polypeptides which may be modified in the PSII system include, but are not limited to D1, D2, PsbO or CP43. Two temperature-sensitive photosystem II mutants of pea are disclosed in Physiologia Plantarum, Volume 49 Issue 2, Pages 135-140, 28 Apr. 2006.

Amino acid substitutions may be selected according to the available structure of PSII. The modified subunits may be generated by site-directed mutagenesis. The resulting DNA may be introduced to the cyanobacterial genome by known techniques such as homologous recombination or via an expression construct.

Systems which may exploit such polypeptides are further described herein below.

As mentioned, hydrogenase enzymes present in cyanobacteria are capable of accepting electrons from photosystem I (PSI) and conversion thereof into hydrogen gas. One limitation of this process is that the endogenous electron carriers donate their electrons to destinations other than hydrogenase. For example, reduced electron carriers, such as ferredoxin also donate electrons to ferredoxin-NADP$^+$-reductase (FNR) enzyme.

In order to increase hydrogen production, electrons may be encouraged to shuttle towards hydrogenase at the expense of the competing processes. International Patent application WO2009/013745 teaches novel hydrogenase polypeptides which are artificially linked to a heterologous ferredoxin. Such polypeptide conceivably force the flow of electrons from an electron donor such as photosystem I (PSI) directly to the hydrogenase at the expense of FNR.

Thus, another contemplated modification of the cyanobacterial cells of the present invention is the expression of engineered Ferredoxin-hydrogenase fusion proteins such as described in International Patent application WO2009/013745 so as to further boost the hydrogen evolution capacity of the engineered organism.

As used herein, the phrase "hydrogenase enzyme" refers to an amino acid sequence of a hydrogenase enzyme with the capability of catalyzing hydrogen oxidation/reduction. Thus the present invention contemplates full-length hydrogenase as well as active fragments thereof. According to one embodiment, the hydrogenase enzyme is a Fe only hydrogenase. According to another embodiment, the hydrogenase is a Ni—Fe hydrogenase. According to yet another embodiment, the hydrogenase is a non-metal hydrogenase. Exemplary hydrogenase enzymes which may be used in accordance with the present invention are set forth by EC 1.12.1.2, EC 1.12.1.3, EC 1.12.2.1, EC 1.12.7.2, EC 1.12.98.1, EC 1.12.99.6, EC 1.12.5.1, EC 1.12.98.2 and EC 1.12.98.3.

As used herein, the term "ferredoxin" refers to an amino acid sequence of the iron sulfur protein that is capable of mediating electron transfer to hydrogenase. Thus the present invention contemplates full-length ferredoxin as well as active fragments thereof. According to a preferred embodiment of this aspect of the present invention, the ferredoxin is a plant-type ferredoxin.

Exemplary ferredoxin polypeptides that may be used in accordance with the present invention include, but are not limited to cyanobacterial ferredoxins, algae ferredoxins and non photosynthetic organism ferredoxins.

The qualifier "heterologous" when relating to the ferredoxin indicates that the ferredoxin is not naturally associated with (i.e. endogenous to) the hydrogenase of the present invention. Thus, for example, the phrase "hydrogenase attached to a heterologous ferredoxin" does not comprise the Fe-only hydrogenase from *clostridium pasteurianum*.

Amino acid sequences of exemplary hydrogenase-ferredoxin polypeptides are set forth in SEQ ID NOs: 15-20.

Exemplary nucleic acid sequences which may be used to express the hydrogenase-ferredoxin polypeptides are set forth in SEQ ID NOs: 21-26.

As mentioned herein above, the endogenous electron transport system in all photosynthetic organisms comprises donation of electrons from ferredoxin to ferredoxin-NADP$^+$-reductase (FNR). In order to divert the flow of electrons away from this competing enzyme, the present invention contemplates down-regulation thereof.

The phrase "ferredoxin-NADP$^+$-reductase" as used herein refers to the enzyme as set forth by EC 1.18.1.2. present in photosynthetic organisms.

Downregulation of FNR may be effected on the genomic level (using classical genetic approaches) and/or the transcript level. This may be achieved using a variety of molecules which interfere with transcription and/or translation (e.g., antisense, siRNA, Ribozyme, DNAzyme). Other examples of agents which may be used to down-regulate FNR are provided in International Patent application WO2009/013745, incorporated herein by reference.

The modified cyanobacterial cells of the present invention may be placed (cultured) in a reactor which is suitably adapted to collect the hydrogen gas.

FIG. 8 is a schematic illustration of a reactor 100 for producing hydrogen according to an embodiment of the invention. Reactor 100 comprises a vessel 102, in which the modified cyanobacterial cells 104 of embodiments of the present invention are held. The modified cyanobacterial cells 104 comprise genetically modified temperature sensitive PSII, such that the PSII is deactivated at high temperatures (between 60-70° C.). The vessel 102 may also comprise other components such as cell medium 106 to ensure the viability of the cells. Reactor 102 and vessel 102 are preferably fabricated from transparent materials in order to allow penetration of sunlight.

According to one embodiment the vessel 102 is a tubing arranged in a circuit. Vessel 102 comprises a recirculation pump 114 which ensures flow of the cyanobacterial cells through the vessel 102. Typically the speed of rotation is set at about 20 cm per minute. One part of the vessel is placed in a containment 108 being maintained at a temperature of about 60-70° C. It will be appreciated that the exact temperature is set according to the temperature sensitive PSII expressed in the cyanobacterial cells 104 any may vary from 55-80° C. Containment 108 may comprise a heater 116 and a monitor 118 for maintaining the temperature. Another part of the vessel is placed in a containment 110 being maintained at a temperature of about 30-50° C. It will be appreciated that the exact temperature is set according to the temperature sensitive PSII expressed in the cyanobacterial cells 104 any may vary from 25-55° C. Containment 110 may comprise a heater 120 and a monitor 122 for maintaining the temperature. The fraction of the vessel maintained in containment 108 as opposed to containment 110 may be adjusted according to the level of hydrogen required. Containment 108 is maintained as an anaerobic environment (e.g. containing nitrogen gas). Containment 110 is maintained as an aerobic environment. Containment 110 may further comprise organic matter 112. Vessel 102 is fabricated from hydrogen and oxygen permeable plastic such that the gases are able to exit the vessel and enter containments 108 and 110 respectively.

Hydrogen gas can be harvested from the reactor by compression of the nitrogen gas in compartment 108.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Substitution of PsaF and PsaJ by PsaJF Fusion Protein in *Synechocystis* sp.

Materials and Methods

Generation of the PsaJF Construct:

PsaJ was amplified with primers 5580 and 5581 and fused to PsaF fragment amplified with primers 5582 and 5583 (see FIG. 9). The JF fusion gene was than ampified using ~300 bp sequences containing the PsaF promoter and the PsaF down homology to create the entire gene cassette. This 970pb fragment was cloned into pGEM-Teasy. Finally, the fragment was moved into a pET28 vectore in order to introduce the Kan resistance gene into a PstI site that was designed into primr 5584.

5578—GTAAATGCTGGCGAGAGGCCAC—SEQ ID NO: 7.

5579—AAGAATCGTTTCCTTGGTTAAACA—SEQ ID NO: 8.

5580—TGTTTAACCAAGGAAACGATTCTTATG-GACGGTTTGAAATCCTTT—SEQ ID NO: 9.

5581—ACAGGGGTGGAAAAGAAGATCG—SEQ ID NO: 10.

5582—CCCGATCTTCTTTTCCACCCCTGTTCT-TGTGCTGGTGACTTTTTGAT TCCTAGC—SEQ ID NO: 11.

5583—GTCCAGTCAATGCCCAACTGGTTAGCGG—SEQ ID NO: 12.

5584—CCGCTAATTAGTTGGGCATTGACTGCAG-GTGAGATAAAAGATTG GTTGGGA—SEQ ID NO: 13.

Purification of PSI Containing PsaJF:

*Synechocystis* cells were grown under fluorescent light on agar Petri dishes containing BG-11 medium. Colonies were inoculated into 500 ml culture medium containing BG-11. After 6 days growth at 30° C. the culture was diluted into 8 L bottle and grown for 6 additional days (Final OD730—1.6~1.8). The cells were harvested by centrifugation at 6000×g for 20 minutes, resuspended in ~100 ml of cold STN1 (30 mM Tricine pH8, 15 mM NaCl, 0.4 M sucrose). The cells were sedimented by centrifugation at 25000×g for 10 min resuspended in 50 ml STN1 containing protease inhibitors. The suspension was broken 3 times using French Press and unlysed cells and cell debris were removed by centrifugation at 25000×g for 10 minutes. The supernatant was centrifuged at 150000×g for 2 hours and the precipitated membranes were suspended in STN1 to give chlorophyll concentration of 3 mg/ml. Dodecyl maltoside (DM) was added from a stock solution of 10% to a final concentration of 15 mg DM per mg chlorophyll. After incubation on ice for 30 minutes, insoluble material was removed by centrifugation of 150,000×g for 30 minutes. The supernatant was applied on DEAE cellulose column and eluted by a NaCl gradient 15-350 mM (100 ml in each chamber) in buffer containing 0.2% DM, 30 mM Tricine pH8. To the green fractions 50% PEG 4000 was added to give a final concentration of 10%. The suspension was centrifuged at 10,000×g for 5 minutes and the pallet was solubilized in 2 ml of 30 mM Tricine, 0.005% DM, 15 mM NaCl. The solution was loaded on sucrose gradient 10-40% in 15 mM NaCl, 30 mM Tricine, 0.005% DM centrifuged in SW40 rotor at 32,000 rpm for 16 hours. The apparent PSI-trimer band was collected and the PSI was precipitated by 10% PEG 6000. After centrifugation the pellet was suspended in 2 mM MES pH6.5, 0.002% DM to give 3 mg chl/ml and subjected to crystallization.

Crystallization of the PsaJF Fusion Protein:

PEG/Ion screen (Hampton) was used for initial screening and the following condition yielded crystals:

7—50 mM Calcium Chloride diydrate 5% PEG 3350, pH5.1
20—50 mM Magesium formate dihydrate 5% PEG 3350, pH7
25—50 mM Magesium acetate tetrathydrate 5% PEG 3350, pH7.9
37—Potassium sodium tartarate tetrahydrate 5% PEG 3350, pH7.4
48—50 mM Ammonium citrate dibasic 5% PEG3350, pH5.1
4—50 mM Sodium malonate pH5, 5% PEG3350

Additional conditions that gave crystals:

MemSys—diluted 1/3
5—33 mM NaCl LiSO$_4$, 33 mM NaCltrate pH5.5, 10% PEG400.
10—33 mM NaCl LiSO$_4$, 33 mM MES pH6.5, 10% PEG400.
11—33 mM NaCl MgCl$_2$, 33 mM MES pH6.5, 10% PEG400.
17—33 mM NaCl LiSO$_4$, 33 mM HEPES pH7.5, 10% PEG400.
18—33 mM NaCl MgCl$_2$, 33 mM HEPES pH7.5, 10% PEG400.
29—33 mM NaCl MgCl$_2$, 33 mM NaCltrate pH5.5, 4.5% PEG4000.
35—33 mM NaCl MgCl$_2$, 33 mM MES pH6.5, 4.5% PEG4000.
41—33 mM NaCl LiSO$_4$, HEPES pH7.5, 4.5% PEG4000.
46—33 mM NaCl MgCl$_2$, 33 mM Tris pH8.5, PEG4000.

MemStart—diluted 1/3
9—33 mM ammonium dihydrogen phosphate pH6.5.
21—33 mM NaCl, Na$_3$-Citrate pH5.6, 10% PEG400
23—33 mM LiSO$_4$, 33 mM ADA pH6.5, 10% PEG400
26—70 mM Na$_3$-Citrate, 33 mM Tris pH8.5, 10% PEG400
33—33 mM NaCl, 33 mM HEPES pH7.5, 4.5% PEG4000
34—33 mM ammonium sulfate, 33 mM HEPES pH7.5, 4.5% PEG4000.
35—70 mM MgCl$_2$, 33 mM Tris pH8.5, 4.5% PEG4000.

Analysis of Rates of Electron Donation by Respiratory Cytochromes

The procedure is described in the legend for FIG. 5.

Results

In order to fuse the PsaJ and PsaF subunits a plasmid was constructed, which contained 300 bp of homology downstream to PsaF and upstream to PsaJ (FIG. 5A). The PsaJ ORF was placed under the control of the PsaF promoter and fused to amino acids 44-165 of PsaF. This fusion protein closely resembles the JF fusion protein found in the phage genome (Sharon, I., Alperovitch, A., Rohwer, F., Haynes, M. Glaser, F. Atamaa-Ismaeel, N., Pinter, R. Y., Partensky, F., Koonin, E. V., Wolf, Y. I., Nelson, N. and Oded Béjà, O. (2009). Photosystem I gene cassettes are present in marine virus genomes. Nature 461, 258-262). To facilitate isolation of transformants, the Kan resistance gene was cloned downstream to the fusion protein. After transformation of *Synechocystis*, Kan resistance colonies were selected and streaked for several times to ensure the correct segregation of the mutant allele. Correct integration and replacement of the wild type genes was verified by PCR using primers that lay outside of the replaced segment.

Following strain construction, the fusion protein was analyzed for effects on stability of and/or the assembly of PSI.

In order to investigate this PSI was purified from wild type and mutant cultures using DEAE chromatography followed by sucrose gradient. As seen in FIG. 5B, there is no change in the relative amounts of trimeric to monomeric forms of the enzyme. Identical results were obtained when soluble membranes were applied directly to the sucrose gradient (data not shown). This shows that the JF fusion protein does not affect the stability of this trimeric supercomplex.

The subunit composition of the complex was examined by SDS-PAGE analysis of the trimeric fractions collected from the sucrose gradient (FIG. 5C). In the gel, a clear band can be seen in the expected location of the fusion protein which represents the successful integration of the fused protein into the PSI complex.

The purified mutant PSI was crystallized and several conditions yielded crystals. FIG. 6 depicts one of the wells containing crystals. Crystals from this first attempt were analyzed in the SLS synchrotron and they diffracted to 8 Å resolution.

The isolated PsaJF mutant PSI was analyzed for the rates of electron donation by respiratory cytochromes. As shown in FIG. 7 horse heart cytochrome c donated electrons to the PsaJF mutant PSI over 5 fold faster than to the wild-type PSI. This experiment shows that, as proposed, the PsaJF mutant PSI is indeed promiscuous for electron donors. Since the mutant cells grew as well as the wild-type cells the promiscuous PSI is not deleterious to the overall photosynthetic process.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of producing hydrogen gas, the method comprising culturing a cyanobacterial cell under conditions that generate hydrogen gas in the cyanobacterial cell, wherein said cyanobacterial cell comprises a PSI complex which accepts electrons from cytochrome C or cytochrome M, wherein said PS 1 Complex comprises a fusion protein which comprises a *Synechocystis* PsaJ polypeptide fused to a *Synechocystis* PsaF polypeptide, wherein said PsaF comprises an N terminal truncation, wherein an amino acid sequence of said fusion protein is at least 80% identical to SEQ ID NO: 1, thereby producing hydrogen gas.

2. The method of claim 1, further comprising harvesting the hydrogen gas following said culturing.

3. The method of claim 1, wherein said cyanobacterial cell is thermophilic.

4. The method of claim 1, wherein said PsaJ is attached to said PsaF by a peptide linker.

5. The method of claim 1, wherein the cell further comprises a polypeptide which comprises a hydrogenase enzyme fused to a heterologous ferredoxin.

6. The method of claim 5, wherein said hydrogenase enzyme is an algal Fe-only hydrogenase.

7. The method of claim 5, wherein said heterologous ferredoxin is a plant ferredoxin.

8. The method of claim 5, wherein said hydrogenase enzyme fused to a heterologous ferredoxin has an amino acid sequence selected from the group consisting of SEQ ID NOs: 20-25.

9. The method of claim 1, wherein the cell produces hydrogen at a temperature above 55° C.

10. The method of claim 1, wherein the cell is a *Mastigocladus laminosus* cell or a *Synechococcus elongates* cell.

* * * * *